United States Patent [19]
Komeda et al.

[11] Patent Number: 6,001,590
[45] Date of Patent: Dec. 14, 1999

[54] **PROMOTER AND TERMINATOR SEQUENCES OF FORMATE DEHYDROGENASE GENE OF *CANDIDA BOIDINII***

[75] Inventors: Toshihiro Komeda; Hisako Suda; Yukio Tamai; Akihiro Iwamatsu, all of Kanagawa; Nobuo Kato; Yasuyoshi Sakai, both of Kyoto, all of Japan

[73] Assignee: Kirin Beer Kabushiki Kaisha, Tokyo, Japan

[21] Appl. No.: 08/817,926

[22] PCT Filed: Sep. 12, 1996

[86] PCT No.: PCT/JP96/02597

§ 371 Date: May 9, 1997

§ 102(e) Date: May 9, 1997

[87] PCT Pub. No.: WO97/10345

PCT Pub. Date: Mar. 20, 1997

[30] Foreign Application Priority Data

Sep. 12, 1995 [JP] Japan ..................................... 7-234133
Feb. 29, 1996 [JP] Japan ..................................... 8-042536

[51] Int. Cl.⁶ ............................. C12N 1/15; C12N 15/31; C12N 15/81; C12P 21/00
[52] U.S. Cl. ..................... 435/69.1; 435/171; 435/252.3; 435/254.2; 435/320.1; 536/24.1
[58] Field of Search ................................ 435/171, 320.1, 435/69.1, 252.3, 254.2; 536/24.1

[56] References Cited

FOREIGN PATENT DOCUMENTS 0 299 108  1/1989  European Pat. Off. .

OTHER PUBLICATIONS

Allen et al., Gene 162:99–104 (1995).

Sakai et al., Journal of Bacteriology 179(14):4480–4485 (1997).

Y. Sakai et al., "Expression of Saccharomyces Adenylate Kinase Gene in *Candida Biodinii* Under the Regualation of its Alcohol Oxidase Promoter", Appl. Microbiol. Biotechnol., vol. 42, (1995), pp. 860–864.

Y. Sakai et al., "Cloning and Sequencing of the Alcohol Oxidase–Encoding Gene (AOD1) from the Formaldehyde–Producing Asporogeneous Methylotrophic Yeast, *Candida Boidinii* S2", Gene, vol. 114, (1992), pp. 67–73.

*Primary Examiner*—Johnny F. Railey, II
*Attorney, Agent, or Firm*—Foley & Lardner

[57] ABSTRACT

A promoter for a formate dehydrogenase gene from *Candida boidinii*, substantially comprising a 190 bp or more continuous nucleotide sequence selected from the nucleotide sequence of SEQ ID NO:1; a promoter for a formate dehydrogenase gene from *Candida boidinii*, substantially comprising the nucleotide sequence of SEQ ID NO:1, 48, 49 or 50; a terminator for a formate dehydrogenase gene from *Candida boidinii*, substantially comprising the nucleotide sequence of SEQ ID NO:2; a gene expression cassette comprising said promoter, a heterologous gene and said terminator; a recombinant expression vector comprising said gene expression cassette; a transformant transformed with said recombinant expression vector; a process for producing an expression product of a heterologous gene, which comprises culturing said transformant and recovering an expression product of a heterologous gene from the culture.

15 Claims, 10 Drawing Sheets

FIG. 10

| Promoter Region Length (bp) | Plasmid | Acid Phosphatase Activity (%) | |
|---|---|---|---|
| | | ME medium | GF medium |
| 1478 | pPUF1 | 100 | 100 |
| 1215 | pPUF15 | 101 | 99 |
| 1000 | pPUF24 | 93 | 99 |
| 839 | pPUF44 | 85 | 94 |
| 819 | pPUF819 | 63 | 94 |
| 801 | pPUF801 | 36 | 94 |
| 779 | pPUF779 | 27 | 91 |
| 756 | pPUF56 | 25 | 92 |
| 690 | pPUF54 | 23 | 91 |
| 668 | pPUF668 | 18 | 90 |
| 642 | pPUF642 | 18 | 85 |
| 622 | pPUF622 | 14 | 21 |
| 602 | pPUF602 | 14 | 21 |
| 403 | pPUF79 | 15 | 21 |
| 228 | pPUF308 | 14 | 18 |
| 194 | pPUF194 | 13 | 20 |
| 161 | pPUF161 | 4 | 5 |
| 115 | pPUF310 | 4 | 3 |
| | parent strain | 4 | 4 |

6,001,590

PROMOTER AND TERMINATOR SEQUENCES OF FORMATE DEHYDROGENASE GENE OF CANDIDA BOIDINII

This application is a national stage application of PCT/JP96/02597 filed on Sep. 12, 1996, the entire contents of which are hereby incorporated by reference, which receives priority from JP 7-234133 filed Sep. 12, 1995 and from JP 8-42536, filed Feb. 29, 1996.

TECHNICAL FIELD

The present invention relates to a promoter and/or a terminator for a formate dehydrogenase gene from *Candida boidinii,* a gene expression cassette containing the promoter, a heterologous gene and the terminator, a vector comprising the expression cassette, transformant cells carrying the expression vector and a process for producing a useful gene product by use of the transformant cells.

BACKGROUND ART

Methanol-assimilating yeasts are those capable of growing on methanol as a sole carbon source. In the first reaction of the methanol metabolism in the methanol-assimilating yeasts, formaldehyde and hydrogen peroxide are produced from methanol and oxygen by alcohol oxidase.

The hydrogen peroxide produced is decomposed by catalase into water and oxygen. The formaldehyde, on the other hand, is oxidized into carbon dioxide by formaldehyde dehydrogenase, S-formylglutathione hydrolase and formate dehydrogenase, and NADH produced in these reactions is utilized as an energy source for cells. Simultaneously, the formaldehyde is condensed with xylulose-5-phosphate by dihydroxyacetone synthase to be converted into glyceraldehyde-3-phosphate and dihydroxyacetone which are then converted to cell constituents via the pentose phosphate pathway.

When the methanol-assimilating yeasts are cultured in the presence of methanol, the above-mentioned alcohol oxidase, dihydroxyacetone synthase and formate dehydrogenase are produced in significant amounts and their contents reach about 40% of the intracellular soluble proteins.

Because a large scale cultivation of the methanol-assimilating yeasts can be done with inexpensive methanol as described above, and because they possess methanol inducible promoters with a strong transcriptional activity not observed in other yeasts, the methanol-assimilating yeasts can be considered to be yeasts suitable for a heterologous gene expression system.

*Candida boidinii* is one of the methanol-assimilating yeasts, and this yeast is used for studying a method of expressing a heterologous gene by use of a regulatory region of an alcohol oxidase gene (AOD1) (Japanese Patent LOP Publication No. 344,895/1993).

Formate dehydrogenase, like alcohol oxidase, is an enzyme produced in a significant amount, but it is an enzyme located downstream in the methanol metabolism and considered to undergo expression regulation different from that of alcohol oxidase. For example, formate dehydrogenase can, as revealed in the present invention, be induced and expressed depending on culture conditions, even in the presence of glucose by which alcohol oxidase expression is completely inhibited. Therefore, it is expected that a method of expressing a large amount of a heterologous gene, which is different from a method using an alcohol oxidase promoter, can be established.

However, no knowledge of the expression and regulation of formate dehydrogenase from *Candida boidinii* has been gained up to now. There is a need for a promoter for formate dehydrogenase to elucidate the expression and regulation of said enzyme and to express a heterologous gene efficiently by its strong transcriptional activity.

DISCLOSURE OF THE INVENTION

The object of the present invention is to provide a promoter and/or a terminator with a strong transcriptional activity to express a heterologous gene, an expression vector containing the promoter and terminator, a transformant carrying the expression vector and a process for producing an expression product of a heterologous gene by use of the transformant.

The present inventors did extensive research to elucidate the expression system of a formate dehydrogenase gene from a methanol-assimilating yeast *Candida boidinii* in order to effectively express a heterologous gene, and as a result, they found a promoter and/or a terminator with a strong transcriptional activity for expressing a heterologous gene, to arrive at the completion of the present invention.

That is, the present invention is a promoter for the formate dehydrogenase gene from *Candida boidinii,* which comprises substantially a 190 bp or more continuous nucleotide sequence selected from the nucleotide sequence of SEQ ID NO:1. Further, the present invention is a promoter for the formate dehydrogenase gene from *Candida boidinii,* which comprises substantially the nucleotide sequence of SEQ ID NO:1, 48, 49 or 50.

Further, the present invention is a terminator for the formate dehydrogenase gene from *Candida boidinii,* which comprises substantially the nucleotide sequence of SEQ ID NO:2.

The phrase "substantially comprises the nucleotide sequence" means that the nucleotide sequence of SEQ ID NO:1, 48, 49, 50 or 2 may have undergone mutations such as replacement, deletion or insertion insofar as the desired promoter and/or terminator activity can be obtained. For example, the sequence of SEQ ID NO:1 in which "C" at position 3 have been replaced by "G" is also intended to fall under the scope of the present invention if the desired promoter activity can be obtained.

Further, the present invention provides a gene expression cassette comprising the promoter, a heterologous gene and the terminator. In the present invention, the "heterologous gene" refers to a gene to be expressed and includes an arbitrary gene heterologous other than the formate dehydrogenase gene derived from *Candida boidinii.* Examples of such heterologous genes include those for acid phosphatase, α-amylase, various interferons, erythropoietin, granulocyte colony stimulating factor etc. Such genes may be obtained in any method.

Further, the present invention provides recombinant expression vectors comprising the gene expression cassette.

Further, the present invention provides transformants transformed with the recombinant expression vector.

Further, the present invention provides processes for producing an expression product of a heterologous gene, which comprise culturing the transformants and recovering an expression product of a heterologous gene from the culture. The medium herein used includes that containing at least one compound having an oxygen or nitrogen atom having at least one C1 substituent group bound to the atom. The compound having an oxygen atom includes e.g. methanol or formic acid or salts thereof, and the compound having a nitrogen atom includes at least one member selected from the group consisting of methylamine, dimethylamine, trimethylamine and a N-substituted-methyl-containing ammonium compound such as choline.

Hereinafter, the present invention is described in detail.

To solve the above problem, the present inventors elucidated the nucleotide sequence of the formate dehydrogenase (FDH) gene from *Candida boidinii* as well as its promoter and terminator in the step (1), isolated the promoter and terminator in the step (2) and constructed an expression vector in the step (3). Further, the present inventors prepared transformed cells with the expression vector, and it was confirmed that the expression of a heterologous gene was induced by methanol etc. as with the formate dehydrogenase gene derived from *Candida boidinii* in the step (4) to arrive at the completion of the present invention.

(1) Cloning of Formate Dehydrogenase Gene

The first step of preparing the gene of the present invention is to clone the formate dehydrogenase gene. Its source includes yeasts such as *Candida boidinii* S2 AOU-1.

The cloning step in the present invention can be carried out in a conventional method (Molecular Cloning (1989), Methods in Enzymology 194 (1991)).

Specifically, the cloning step can be carried out as follows: (a) a gene library of said yeast is prepared by extracting the total DNA from said yeast and transforming a host with DNA fragments derived from said DNA using a vector, and (b) a desired clone is selected from this gene library, followed by amplification of the clone.

(a) Preparation of Gene Library of the Yeast

The extraction of the total DNA from said yeast involves preparing e.g. a yeast protoplast and then subjecting the protoplast to a conventional method such as DNA extraction, removal of cell residues at high salt concentration and subsequent alcohol precipitation, phenol or/and chloroform extraction and subsequent alcohol precipitation, or the like. Although DNA can be extracted directly by disrupting cells with glass beads etc. without previously preparing a protoplast, the above protoplast method is preferably carried out for easiness of preparation of high-molecular-weight DNA.

A genomic library can be obtained by partially digesting the resulting chromosomal DNA with suitable restriction enzymes (e.g. Sau3AI), then ligating them to a suitable vector, and transforming the mixture into a suitable host. As the vector, it is also possible to employ commercially available plasmids such as pBR family, pUC family, Blue Script family etc. which are known vectors for use in the preparation of a conventional gene library. It is further possible to employ a wide range of phage vectors such as Charon family and EMBL family as well as cosmids etc.

The host to be transformed or transduced with the vector prepared for preparation of the gene library can be selected depending on the type of the vector.

(b) Selection of Clone

A clone containing the target formate dehydrogenase gene can be selected from the above gene library by techniques such as colony hybridization, plaque hybridization etc. using a labeled probe containing a unique sequence from the target formate dehydrogenase gene. The unique sequence as the probe in the formate dehydrogenase gene can be obtained by synthesizing an oligonucleotide corresponding to a partial amino acid sequence of formate dehydrogenase purified from *Candida boidinii* and specifically amplifying the desired DNA fragment by PCR using the genomic DNA of *Candida boidinii* as a template (PCR Technology, Henry A. Erlich, Atockton Press (1989)). The synthesized oligonucleotide can also be used as the probe.

The determination and confirmation of the nucleotide sequence of the target gene obtained in above manner can be carried out using e.g. the chemical modification method of Maxam-Gilbert (Maxam-Gilbert, Methods in Enzymology, 65, 499 (1980)), the dideoxynucleotide chain termination method (Messing, J. and Vieire, J., Gene, 19, 269 (1982)) or their automated modified methods.

Once the nucleotide sequence is determined, the target gene can be obtained by chemical synthesis or by PCR using a synthetic primer based on the determined nucleotide sequence, or by hybridization to a DNA fragment having said nucleotide sequence as the probe.

(2) Isolation of Promoter and Terminator Region

To remove the promoter and terminator region, they can be cleaved off with restriction enzymes. Generally speaking, however, suitable restriction enzyme sites are not necessarily located at suitable sites. Hence, there is a method in which a fragment containing e.g. the promoter is cleaved with an endonuclease in the direction toward the promoter from a restriction enzyme site in the coding region to a suitable site before the promoter, and then clones with a suitably cleaved fragment are selected. Recently, the target promoter and terminator region can be easily obtained by PCR amplification with primers in which a restriction enzyme site is provided at their terminals.

Alternatively, these regions can also be chemically synthesized, or a semisynthetic promoter or terminator can also be constructed by using a chemically synthesized and cloned partial region and a restriction enzyme site.

The present promoter region includes the sequence of SEQ ID NO:1 to which however it is not limited and the nucleotide sequence can be modified by deletion, insertion, replacement, addition etc., if it substantially has a transcriptional activity.

The modification of the nucleotide sequence can be carried out using well-known mutagenesis methods (e.g. methods using TAKARA LA PCR in vitro Mutagenesis kit).

The promoter of the present invention substantially contains a 190 bp or more continuous nucleotide sequence in the nucleotide sequence of SEQ ID NO:1 and is involved in the expression of the formate dehydrogenase gene from *Candida boidinii*. This 190 bp or more continuous nucleotide sequence may lack a part or the whole of the 3'- and/or 5'-terminals of the nucleotide sequence of SEQ ID NO:1. For example, the promoter substantially containing the nucleotide sequence (642 bp) of SEQ ID NO:49 can be obtained by deleting the 5'-terminal region (positions 1 to 836) from the nucleotide sequence of SEQ ID NO:1. Similarly, the promoter substantially containing a 300 bp continuous nucleotide sequence can be obtained by deleting the 5'-terminal region (positions 1 to 600) and the 3'-terminal region (positions 901 to 1478) from the nucleotide sequence of SEQ ID NO:1.

It is appropriate to employ PCR using e.g. a commercial deletion kit (deletion kit for kilosequence, available from Takara Shuzo Co., Ltd.) in order to prepare the promoter of the present invention from which such broad regions have been deleted.

(3) Construction of Expression vector

The expression vector of the present invention can be obtained by inserting the FDH promoter, a heterologous gene, the FDH terminator, a marker gene, and a homologous region into a suitable vector. The vector used include *E. coli* plasmid vectors such as the above-mentioned pBR family, pUC family, Blue Script family etc. The insertion of the above components into the vector can easily be carried out by those skilled in the art in light of the following description in Examples or conventional techniques. The selective marker gene and the homologous region can be easily determined by those skilled in the art. The marker gene includes resistance genes against antibiotics such as G-418 etc. and genes that complement auxotrophies such as URA3, LEU2 etc.

(4) Transformation

To introduce the plasmid into the yeasts in question, general methods for transforming yeasts can also be used. Examples of such methods are the protoplast method, lithium method, electroporation method and their modified methods. The expression vector of the present invention can be integrated into host genomic DNA and maintained stably in it. The expression vector is also allowed to be present as a plasmid by use of a known method (Sakai, Y. et al., J. Bacteriol., 175, 3556 (1993)).

(5) Production of Gene Expression Product

In the following, methods of producing the gene expression product are described.

In the present invention, the gene expression product is obtained by culturing the transformant obtained as described above and then purifying the gene expression product from the culture.

A compound containing an oxygen or nitrogen atom with at least one C1 substituent group bound to the atom can be added to the culture medium. For example, methanol or formic acid or its salt can be added as the oxygen atom-containing compound, and at least one member selected from the group consisting of methylamine, dimethylamine, trimethylamine, and N-substituted-methyl-containing ammonium compounds (e.g. choline) can be added as the nitrogen atom-containing compound.

To induce expression of the gene product by the above compound, the following conditions are used for the medium for culturing the above strain:

For induction of expression of the gene product by methanol, mention may be made of a medium containing, in addition to methanol as a carbon source, one or more nitrogen sources selected from yeast extract, trypton, meat extract, casamino acid, ammonium salt etc., and inorganic salts such as phosphate, sodium, potassium, magnesium, calcium, iron, copper, manganese, cobalt etc., if necessary trace nutrients such as vitamins, nucleotides etc. and sugar raw materials.

For induction of expression of the gene product by formic acid, mention may be made of a medium containing, in addition to formic acid as a carbon source, one or more carbon sources selected from glucose, glycerol etc., one or more nitrogen sources selected from yeast extract, trypton, meat extract, casamino acid, ammonium salt etc., and inorganic salts such as phosphate, sodium, potassium, magnesium, calcium, iron, copper, manganese, cobalt etc., if necessary trace nutrients such as vitamins, nucleotides etc. and sugar raw materials.

For induction of expression of the gene product by methylamine, dimethylamine, trimethylamine or choline, mention may be made of a medium containing, in addition to at least one of these inducers as a nitrogen source, one or more carbon sources selected from glucose, glycerol etc., and inorganic salts such as phosphate, sodium, potassium, magnesium, calcium, iron, copper, manganese, cobalt etc., if necessary trace nutrients such as vitamins, nucleotides etc. and sugar raw materials.

The medium is adjusted preferably to pH 5.5–6.5. The culture temperature is in the range of 25 to 30° C., preferably about 28° C. The culture time ranges from about 24 to 1,000 hours, and the transformant is grown in static culture, shaking culture, stirring culture, or continuous culture under aeration.

After the culture is finished, the gene product can be recovered using conventional protein purification means. For example, the gene product, when produced intracellulary, is extracted by disrupting the transformant in a usual manner by ultrasonication, grinding or under pressure. If necessary, protease inhibitors may be added.

If the gene product is produced in the culture supernatant, the culture liquid itself can be used.

Then, this solution is filtered or centrifuged to remove solids and treated if necessary with protamine etc. to remove nucleic acids.

The solution is then fractionated by adding ammonium sulfate, alcohol, acetone etc., and the resulting precipitates are recovered as a crude protein extract. A purified enzyme preparation can be obtained from the crude protein extract by subjecting its solution to various kinds of chromatography, electrophoresis etc. For example, the target gene product can be purified by suitably selecting or combining fractionation methods using gel filtration using Sephadex, Ultrogel or Bio-Gel, ion-exhange chromatography, electrophoresis using polyacrylamide gel etc., affinity chromatography, and reverse phase chromatography etc. However, the above culture methods and purification methods are described merely for illustrative purposes and should not be construed as restrictive.

The amino acid sequence of the gene product thus purified can be determined using any of the conventional amino acid analysis methods, e.g. automatic amino acid sequencing methods including the Edman degradation method.

BRIEF DESCRIPTION OF THE DRAWINGS

FIG. 10 shows acid phosphatase activity regulated by an 5'-deletion derivatives of FDH promoter. In FIG. 10, the relative activities of transformants carrying respective plasmids are shown as relative values to the activity (as 100%) of a transformant carrying plasmid pPUF1 containing the entire promoter region. The "parent strain" is *Candida boidinii* KST2515 into which no plasmid was introduced.

BEST MODE FOR CARRYING OUT THE INVENTION

Figure 1:
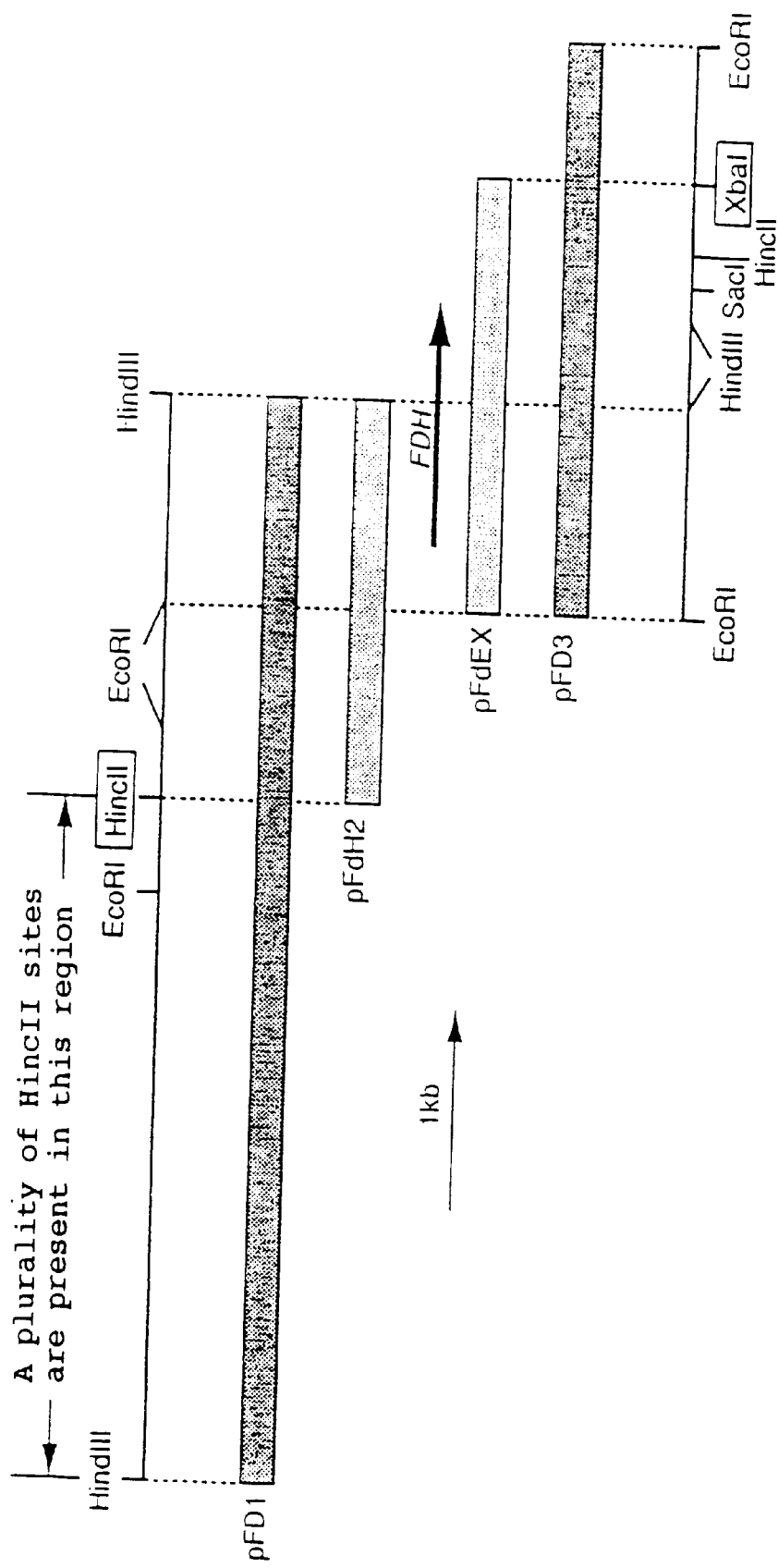
FIG. 1 shows restriction enzyme maps of formate dehydrogenase gene-containing plasmids.

The present invention is described in more detail by reference to Examples to which however, the present invention is not limited.

EXAMPLE 1

Cloning of FDH Gene from *Candida boidinii*

In this example, a formate dehydrogenase gene was obtained from *Candida boidinii* S2 AOU-1 (Tani, Y. et al., Agri. Biol. Chem., 49, 2699 (1985)) and its nucleotide sequence was determined. Said strain was designated *Candida boidinii* SAM1958 and deposited as FERM BP-3766 on Feb. 25, 1992, with the National Institute of Bioscience and Human-Technology, Agency of Industrial Science and Technology, Japan.

(1-1) Construction of Probe

The N-terminal amino acid sequence of formate dehydrogenase from *Candida boidinii* was determined to be the sequence shown in SEQ ID NO:3 by gas feed peptide sequencer model 120-A (Applied Biosystem). According to a method described by Iwamatsu ("Seikagaku" (Biochemistry), 63, 139 (1991)), its partial amino acid sequences were determined as shown in SEQ ID NOS:4 to 16.

An oligonucleotide (FDH-NT1) corresponding to the N-terminal amino acid sequence of from amino acid 8 (tyrosine) to amino acid 14 (alanine) in SEQ ID NO:3 and an oligonucleotide (FDH-AP7) corresponding to the amino acid sequence of from amino acid 5 (glycine) to amino acid 12 (tyrosine) in SEQ ID NO:8 were synthesized respectively with 394 type DNA/RNA synthesizer (Applied Biosystem).

| | |
|---|---|
| FDH-NT1: | SEQ ID NO:17 |
| FDH-AP7: | SEQ ID NO:18 |

The 5'-terminals of primers FDH-NT1 and FDH-AP7 possess a restriction enzyme BamHI recognition site GGATCC i.e. the nucleotide sequence at positions 4 to 9 in SEQ ID NOS:17 and 18. The above primers FDH-NT1 and FDH-AP7 were mixed with *Candida boidinii* genomic DNA prepared according to the method of Cryer et al. (Cryer, D. et al., Methods Cell Biol., 12, 39 (1975)) and the mixture was subjected to 30 cycles of PCR using rTaq polymerase (Takara Shuzo Co., Ltd.), each cycle consisting of reaction at 95° C. for 1 minute, 58° C. for 1 minute and 72° C. for 3 minutes.

An about 900 bp DNA fragment thus amplified was cleaved with BamHI and then cloned in pBluescript II SK+. Its nucleotide sequence was determined in both directions by use of a dye primer cycle sequence kit (Perkin-Elmer). The result agreed with the amino acid sequence used in the primers, indicating that a part of the FDH gene was amplified.

(1-2) Construction of Library and Screening

Genomic DNA from *Candida boidinii* was cleaved with various restriction enzymes and subjected to Southern hybridization where the DNA fragment obtained in item (1-1) above was used as a probe. The probe was labeled with a radioisotope by use of a mega-primer DNA labeling system (Amersham), and the hybridization was carried in a usual manner (Molecular Cloning, 2nd edn., ed. Sambrook, J., et al., Cold Spring Harbor Laboratory U.S.A., 1989).

As a result, a signal was detected in an about 3 kb EcoRI fragment and about 5 kb HindIII fragment. To clone these DNA fragments, a library was constructed.

The genomic DNA from *Candida boidinii* was cleaved with HindIII and then subjected to agarose electrophoresis, and the DNA fragment of about 5 kb was recovered from the gel. The recovered DNA fragment was inserted into the HindIII cleavage site in pBluescript II SK+ to construct a HindIII plasmid library. An EcoRI plasmid library was also prepared in the same manner.

These libraries were screened by colony hybridization. By autoradiography, clones carrying pFD1 and pFD3 were selected as positive clones from the HindIII and EcoRI plasmid libraries respectively.

(1-3) Subcloning

Restriction enzyme maps of plasmids pFD1 and pFD3 were prepared (FIG. 1). It was estimated from analysis by Southern hybridization that the FDH gene is located in an about 3.6 kb region between HincII and XbaI sites (HincII and XbaI are enclosed) in FIG. 1. For the determination of the nucleotide sequence, a 2 kb HincII-HindIII fragment in pFD1 and a 2.5 kb EcoRI-XbaI fragment in pFD3 were inserted respectively into pBluescript II SK− to construct pFdH2 and pFdEX respectively (FIG. 1).

(1-4) Nucleotide Sequencing

Using a deletion kit for kilosequence (Takara Shuzo Co., Ltd.), various deletion derivatives were prepared from plasmids pFdH2 and pFdEX constructed in item (1-3) above. Using a dye primer cycle sequencing kit and a dye terminator cycle sequencing kit (Perkin-Elmer) with above plasmids as templates, the nucleotide sequence was determined. By linking the determined nucleotide sequences of plasmids pFdH2 and pFdEX, the whole nucleotide sequence of the about 3.6 kb HincII-XbaI region shown in FIG. 1 was determined (SEQ ID NO:19).

In the nucleotide sequence of SEQ ID NO:19 there is an open reading frame consisting of 1,095 base pairs beginning from ATG at position 1479 and ending with TAA at position 2573. This open reading frame (SEQ ID NO:20) is evidently the target formate dehydrogenase gene because:

i) The amino acid sequence (SEQ ID NO:51) deduced from the nucleotide sequence agrees with partial amino acid sequences of the purified enzyme (in the sequence of SEQ ID NO:20, amino acid sequences at positions 1 to 45, 56 to 76, 86 to 103, 189 to 201, 206 to 236, 241 to 246, 291 to 326, and 328 to 356);

ii) The molecular weight (41 kDa) of the enzyme estimated by SDS-PAGE agrees with the molecular weight (40,368) calculated from the nucleotide sequence; and iii) The amino acid sequence estimated from the nucleotide sequence has 82% homology with the amino acid sequence of formate dehydrogenase derived from methanol-assimilating yeast *Hansenula polymorpha* (EPO0299108, Jan. 18, 1989). The nucleotide sequences of the 5'-side upstream region (promoter region) and of the 3'-side upstream region (terminator region) have no homology with those from *Hansenula polymorpha* above.

EXAMPLE 2

Construction of Heterologous Gene Expression Cassette (2-1) Isolation of Promoter and Terminator Regions To isolate the promoter and terminator regions from the formate dehydrogenase gene, suitable restriction enzyme sites were provided before the translation initiation codon (ATG) and after the termination codon (TAA). PCR shown in FIG. 4 was used to introduce the restriction enzyme sites. The following 4 oligonucleotides were synthesized as PCR primers:

| PfdhP5: | SEQ ID NO:21 |
|---|---|
| PfdhP3: | SEQ ID NO:22 |
| PfdhT5: | SEQ ID NO:23 |
| PfdhT3: | SEQ ID NO:24 |

PfdhP3 contains the same nucleotide sequence as the 3'-terminal of the FDH promoter and has a NotI restriction enzyme cleavage site at the 5'-terminal (sequence at positions 1 to 8 in SEQ ID NO:22). PfdhT5 contains the same nucleotide sequence as the 5'-terminal of the FDH terminator and has NotI and SmaI restriction enzyme cleavage sites at the 5'-terminal (sequence at positions 1 to 14 in SEQ ID NO:23). PfdhP5 has an AccI restriction enzyme cleavage site (nucleotide at positions 5 to 10 in SEQ ID NO:21) present in the FDH promoter, and PfdhT3 has a SacI restriction enzyme cleavage site (sequence at positions 13 to 18 in SEQ ID NO:24) present in the FDH terminator.

Plasmid pFdH2 containing the FDH promoter region was mixed with primers PfdhP5 and PfdhP3 and the mixture was subjected to PCR ((1 minute at 94° C., 1 minute at 57° C., and 1 minute at 72° C.)×25 cycles) using Ex Taq polymerase (Takara Shuzo Co., Ltd.).

The amplified DNA contains a downstream region from the AccI restriction enzyme cleavage site in the FDH promoter region and has a NotI restriction enzyme cleavage site at the 3'-terminal. The reaction product was subjected to agarose gel electrophoresis, and the amplified DNA was recovered. The recovered DNA fragment was ligated to vector pT7 Blue T-Vector (Novagene) to construct pFP1.

Similarly, plasmid pFdEX containing the FDH terminator region was mixed with primers PfdhT5 and PfdhT3 and the mixture was subjected to PCR ((1 minute at 94° C., 1 minute at 57° C. and 1 minute at 72° C.)×25 cycles), and a DNA fragment containing an upstream region from the SacI restriction enzyme cleavage site in the FDH terminator and having the NotI and SmaI restriction enzyme cleavage sites at the 5'-terminal was amplified. This DNA fragment was ligated to pT7 Blue T-Vector to construct pFT1.

Figure 2:
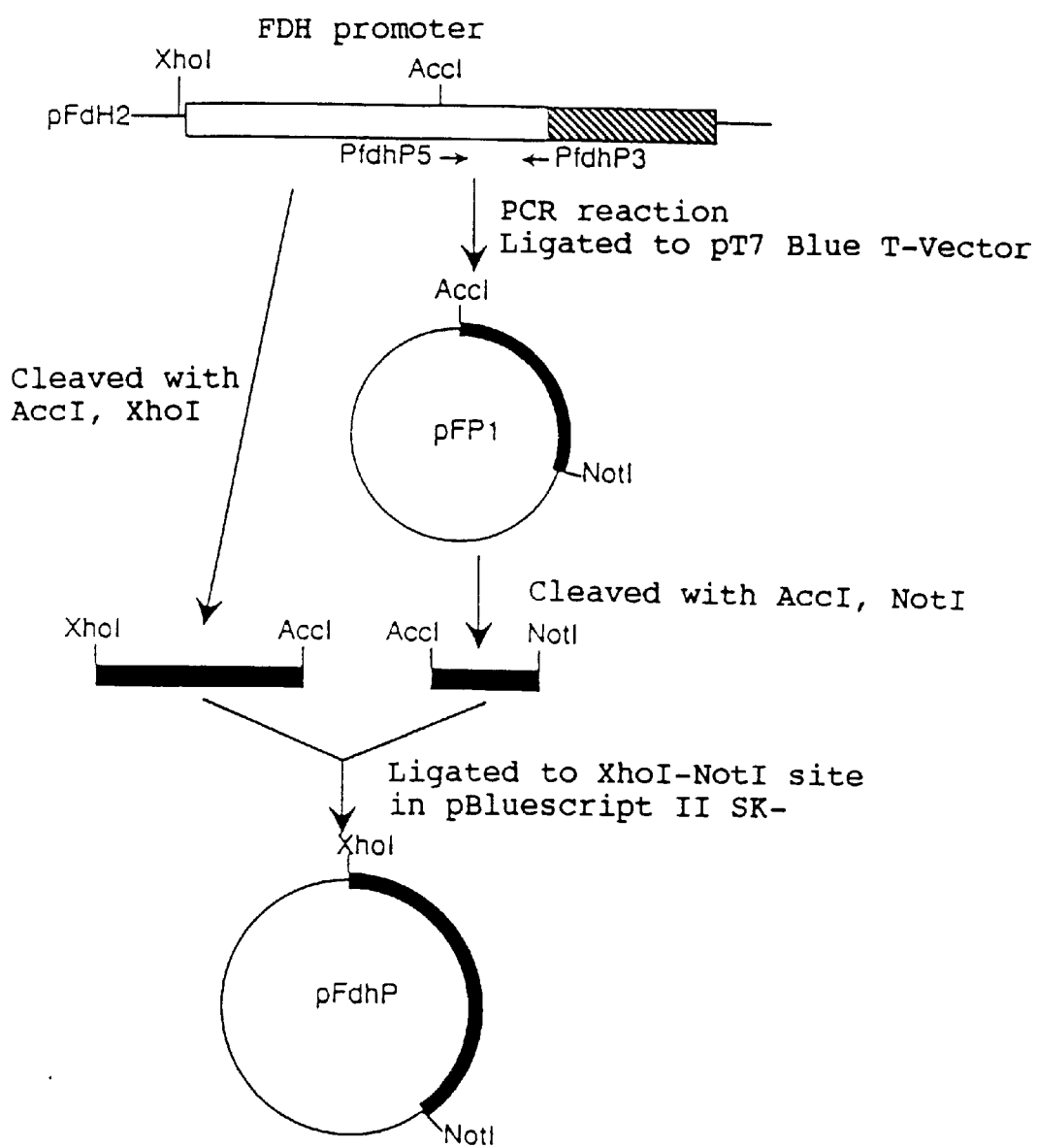
FIG. 2 shows a scheme for constructing a plasmid containing a promoter fragment for the formate dehydrogenase gene by PCR.
Figure 3:
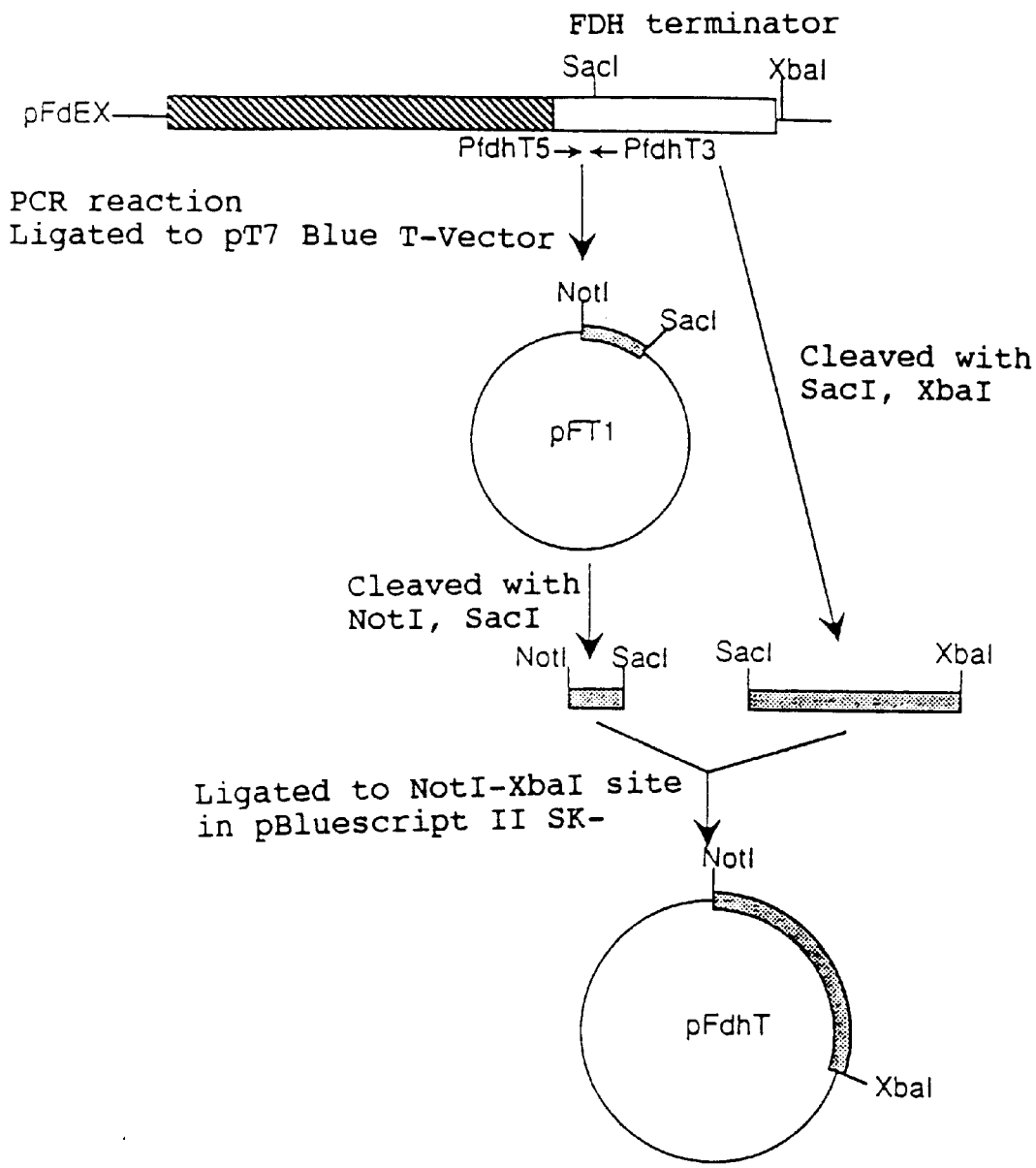
FIG. 3 shows a scheme for constructing a plasmid containing a formate dehydrogenase gene terminator fragment by PCR.

Using a dye primer cycle sequencing kit and a dye terminator cycle sequencing kit (Perkin-Elmer) with above plasmids as templates, the nucleotide sequence was determined, and it was confirmed that the target regions were accurately amplified. Plasmid pFP1 was cleaved with AccI and NotI and then separated by agarose gel electrophoresis to give a 0.5 kb DNA fragment. Plasmid pFdH2 was cleaved with XhoI and AccI and then separated to give a 1 kb DNA fragment containing the FDH promoter region upstream from the AccI site (FIG. 2). The resulting 2 kinds of DNA fragment were inserted into XhoI-NotI site in pBluescript II SK– to construct pFdhP having the FDH promoter region (FIG. 2). Similarly, a 0.15 kb NotI-SacI fragment from plasmid pFT1 and a 0.85 kb SacI-XbaI fragment from plasmid pFdEX were inserted into NotI-XbaI site in pBluescript II SK– to construct pFdhT having the FDH terminator region (FIG. 3).

Figure 4:
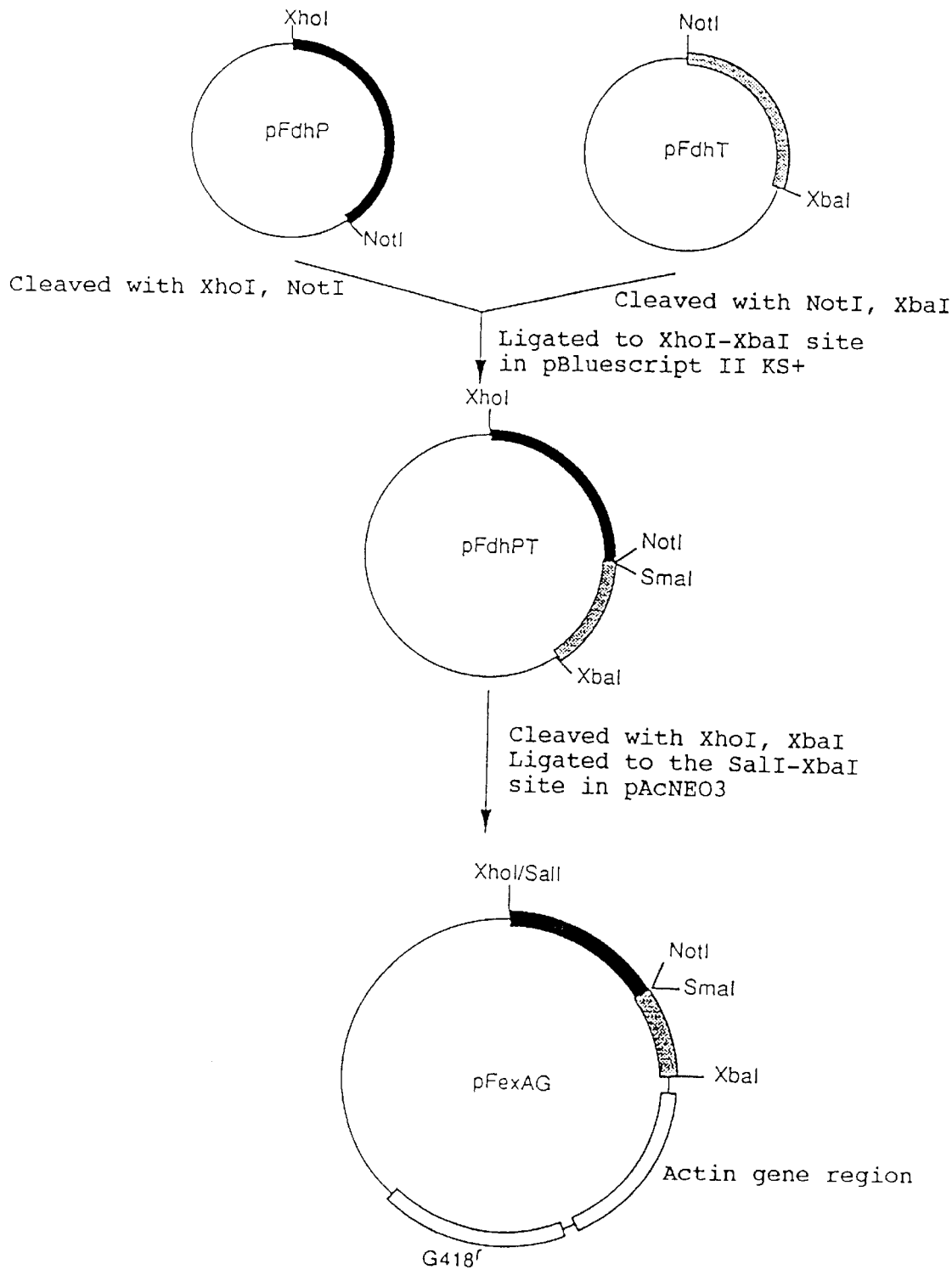
FIG. 4 shows a scheme for constructing an expression plasmid pFexAG using the formate dehydrogenase gene promoter and terminator.

Then, a DNA fragment of the FDH promoter region obtained by cleaving plasmid pFdhP with XhoI and NotI and a DNA fragment of the FDH terminator region obtained by cleaving plasmid pFdhT with NotI and XbaI were inserted into XhoI-XbaI site in pBluescript II KS+ to construct pFdhPT (FIG. 4). pFdhPT has the the FDH gene promoter and terminator regions, and various structural genes (heterologous genes) can be inserted into the site between NotI and SmaI between the promoter and the terminator (FIG. 4).

EXAMPLE 3

Construction of Marker Gene and Homologous Region

A G418 resistance gene expressed using an actin gene promoter and terminator from *Candida boidinii* was used as a marker gene, and an actin gene region was used as a homologous region.

(3-1) Isolation of *Candida boidinii* Actin Gene (3-1-1) Construction of Genomic DNA Library of *Candida boidinii*

Genomic DNA was prepared by a potassium acetate method (Methods in Enzymology, 65, 404 (1980)) from *Candida boidinii* ATCC48180 cultured in a YPD medium (1% yeast extract, 2% peptone, 2% glucose, pH 6.0).

According to the method of Frischauf et al. (Methods in Enzymology, 152, 183, Academic Press 1987), the genomic DNA was partially digested with restriction enzyme Sau3AI and separated by 10–40% sucrose density gradient centrifugation to prepare a 15–20 kb DNA fraction.

As the vector DNA, pUC118 was used. pUC118 was cleaved with restriction enzyme BamHI and then treated with alkaline phosphatase.

100 ng of the above genomic DNA fragment digested partially with Sau3AI and 50 ng of the above pUC118 fragment digested with BamHI were mixed and ligated at 16° C. for 30 min. using a DNA ligation kit (Takara Shuzo Co., Ltd.).

*E. coli* DH5 α competent cells prepared according to the method of Hanahan (Gene, 10, 63 (1980)), were transformed with the above recombinant plasmid to yield about 20,000 transformants.

(3-1-2) Isolation of the Actin Gene

The *Candida boidinii* actin gene was isolated by hybridization to a radioisotope-labeled homologous actin gene from *Saccharomyces cerevisiae*.

The PCR technique was used for preparation of the actin gene from *Saccharomyces cerevisiae*. According to the nucleotide sequence of the known *Saccharomyces cerevisiae* actin gene (Gallwitz, D., Sures, I., Proc. Natl. Acad. Sci., U.S.A., 77, 2546 (1980)), the following 2 kinds of oligonucleotide were synthesized as primers for PCR with 394 type DNA/RNA synthesizer (Applied Biosystem):

| PScAC1: | SEQ ID NO:25 |
|---|---|
| PScAC2: | SEQ ID NO:26 |

Primers PScAC1 and PScAC2 are nucleotide sequences corresponding respectively to the N- and C-terminal side regions in the exon of the actin gene from *Saccharomyces cerevisiae*.

Genomic DNA prepared from *Saccharomyces cerevisiae* S288C was mixed with primers PScAC1 and PScAC2, and the mixture was subjected to PCR ((30 seconds at 94° C., 1 minute at 55° C., and 2 minutes at 72° C.)×25 cycles).

The reaction product was separated by agarose gel electrophoresis, and the amplified DNA fragment was recovered. This DNA fragment was labeled with a $^{32}$P radioisotope using a mega-primer DNA labeling system (Amersham).

Hybridization was carried out at 65° C. for 16 hours in a usual manner (Molecular Cloning, 2nd edn., ed. Sambrook, J., et al., Cold Spring Harbor Laboratory U.S.A., 1989), and the filter was washed twice with 2×SSPE buffer containing 0.1% SDS and once with 1×SSPE buffer containing 0.1% SDS, and positive clones were detected by autoradiography.

Plasmid DNA was extracted from the resulting 4 positive clones by the alkali lysis method (Molecular Cloning, 2nd edn., ed. Sambrook, J., et al., Cold Spring Harbor Laboratory U.S.A., 1989). The resulting plasmid DNA and the genomic DNA from *Candida boidinii* ATCC48180 were cleaved with various restriction enzymes and subjected to Southern hybridization. Comparison of the sizes of the hybridized bands suggested that a clone carrying plasmid pAc1 contained the actin gene region.

(3-1-3) Subcloning

To prepare a restriction enzyme map of the actin gene, plasmid pAc1 was cleaved with restriction enzymes KpnI and SmaI, and the resulting 6 kb fragment carrying the actin gene was inserted into KpnI-SmaI site in pBluescript II KS+ to construct plasmid pAc1-7. A further detailed restriction enzyme map of plasmid pAc1-7 was prepared (see FIG. 5).

Figure 5:
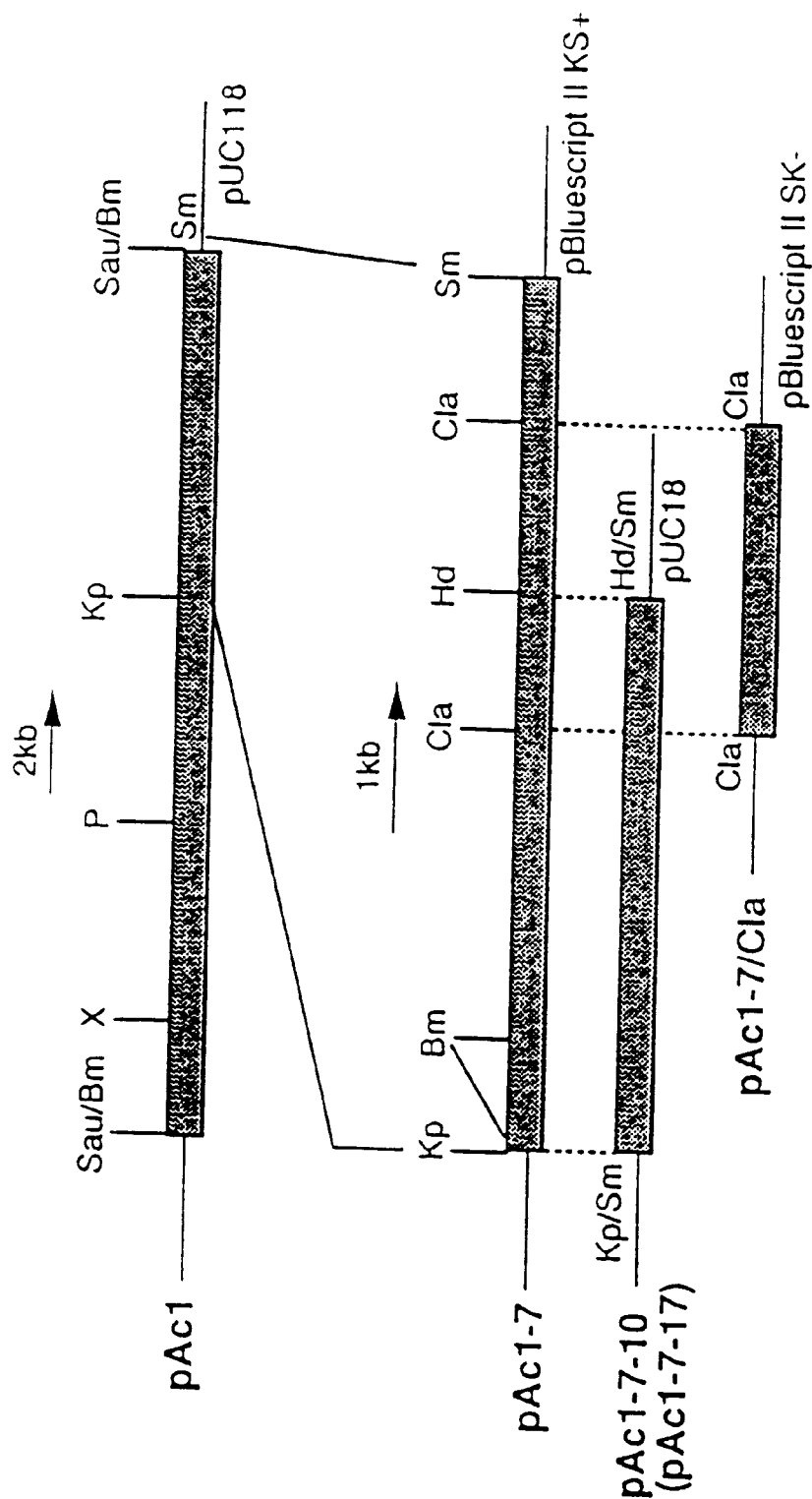
FIG. 5 shows restriction enzyme maps of actin gene-containing plasmids.

It was assumed from analysis by Southern hybridization that the actin gene is located in the about 5 kb KpnI-ClaI region. To determine its nucleotide sequence, further subcloning was carried out. First, pAc1-7 was cleaved with KpnI and HindIII, and an about 3.4 kb fragment was extracted from it, then blunt-ended with T4 DNA polymerase, and inserted into the SmaI site in pBluescript II KS+ to construct plasmids pAc1-7-10 and pAc1-7-17 where the latter contained the insert in the opposite direction. Then, an about 2 kb fragment obtained by cleaving pAc1-7 with restriction enzyme ClaI was inserted into the ClaI site in pBluescript II KS+ to construct plasmid pAc1-7/Cla (FIG. 5).

(3-1-4) Nucleotide Sequencing

Using a deletion kit for kilosequence (Takara Shuzo Co., Ltd.), various deletion derivatives were prepared from plasmids pAc1-7-10, pAc1-7-17, and pAc1-7/Cla. Using a dye primer cycle sequencing kit and a dye terminator cycle sequencing kit (Perkin-Elmer) with above plasmids as templates, the nucleotide sequence was determined. By linking the determined nucleotide sequences of plasmids pAc1-7-10 and pAc1-7/Cla, the whole nucleotide sequence of the about 5 kb KpnI-ClaI region shown in FIG. 5 was determined (SEQ ID NO:27).

From this sequence, the coding region in the actin gene was determined. Using Time Saver cDNA Synthesis Kit, Directional Cloning Toolbox (Pharmacia), cDNA having an EcoRI protruding end at the 5'-terminal and a NotI protruding end at the 3'-terminal was synthesized from mRNA from *Candida boidinii* ATCC48180. Phagemid Direction Cloning Vector (Pharmacia) was used to link the synthesized cDNA to the EcoRI-NotI site in plasmid pT7T3D to prepare a cDNA library. An oligonucleotide primer PCBAC was synthesized on the basis of a 2858 bp to 3558 bp nucleotide sequence in SEQ ID NO:27 having high homology with the actin gene from *Saccharomyces cerevisiae*, and an oligonucleotide primer PT7T3 was synthesized on the basis of the nucleotide sequence upstream from the EcoRI site in vector pT7T3D.

| PCBAC: | SEQ ID NO:36 |
|---|---|
| PT7T3: | SEQ ID NO:37 |

The above cDNA library was mixed with primers PCBAC and PT7T3 and the mixture was subjected to PCR ((30 seconds at 94° C., 1 minute at 55° C., and 30 seconds at 72° C.)×25 cycles) using rTaq polymerase (Takara Shuzo Co., Ltd.).

The reaction product was subjected to agarose gel electrophoresis, and the amplified DNA fragments were recovered. The recovered DNA fragments were ligated to vector pT7 Blue T-Vector. Using a dye primer cycle sequencing kit (Perkin-Elmer) with above plasmids as templates, the nucleotide sequence was determined. The longest nucleotide sequence from the clones started at position 1922 in SEQ ID NO:27, from which the regions at positions 1974 to 2508 and positions 2524 to 2853 were deleted. These deleted regions were intron, and the sequence of ATG (position 1965 in SEQ ID NO:27) appearing first in the cDNA was assumed to an initiation codon. The homology of the obtained gene with the actin gene from *Saccharomyces cerevisiae* was examined with respect to the estimated amino acid sequence of the gene product. Because there was about 96% homology therebetween, it was determined that the obtained gene is the *Candida boidinii* actin gene and that its coding region starts at the nucleotide at position 1965.

Figure 6:
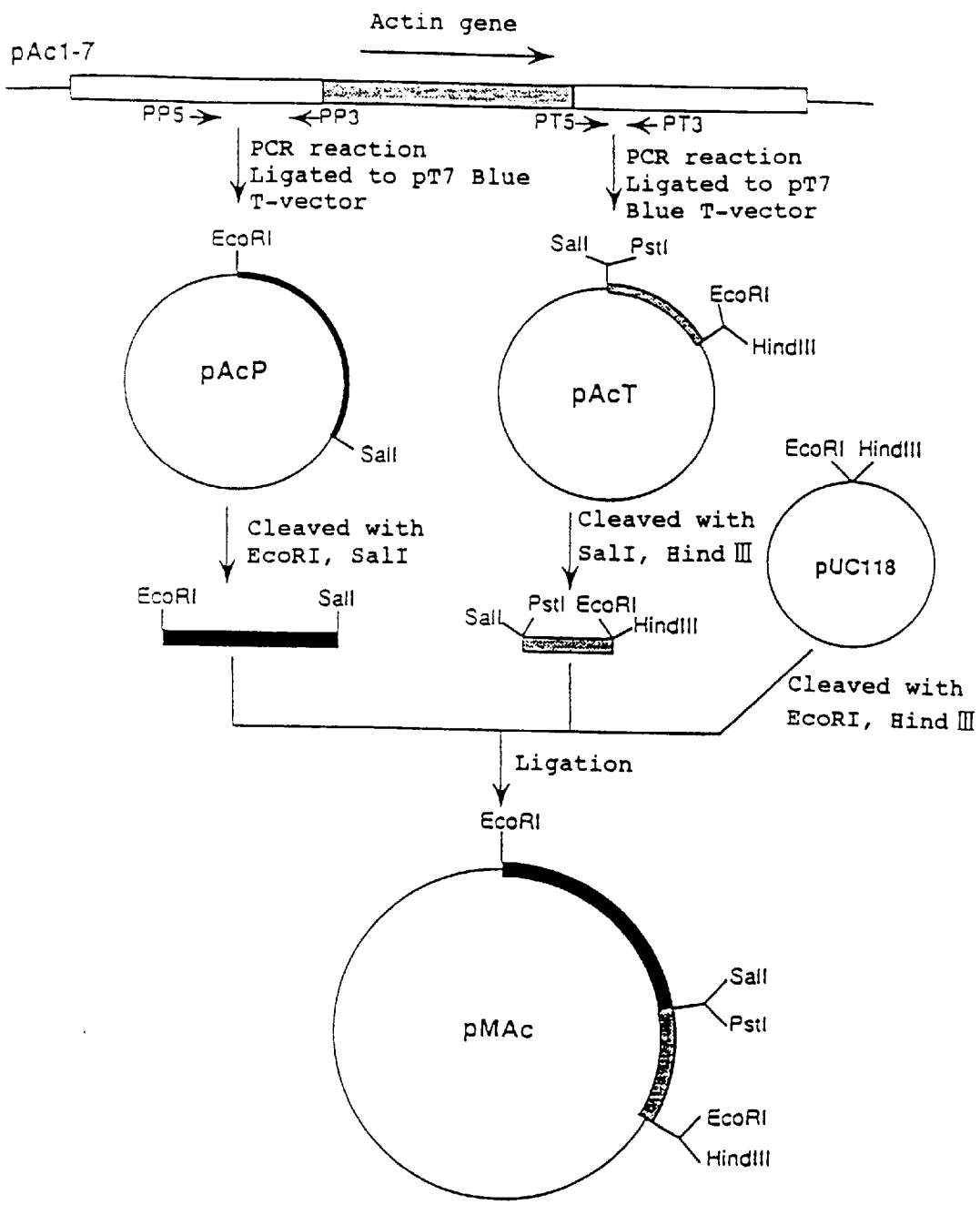
FIG. 6 shows a method of preparing actin gene promoter and terminator fragments by PCR as well as a scheme for constructing an expression plasmid using the promoter and terminator.

(3-2) Construction of Dominant Marker Gene Expression Cassette (3-2-1) Isolation of Promoter and Terminator Region The promoter and terminator region was isolated by the PCR technique (FIG. 6). The following 4 oligonucleotides were synthesized to amplify an about 1 kb region as the promoter region upstream from the replication initiation codon ATG and an about 0.5 kb region as the terminator region downstream from the termination codon TAA.

| PP5: | SEQ ID NO:28 |
|---|---|
| PP3: | SEQ ID NO:29 |
| PT5: | SEQ ID NO:30 |
| PT3: | SEQ ID NO:31 |

PP5 and PP3 contain the 5'- and 3'-terminal nucleotide sequences of the promoter region respectively, and the 5'-terminal of PP5 has a restriction enzyme EcoRI recognition site (sequence at positions 3 to 8 in SEQ ID NO:28), and the 5'-terminal of PP3 has a SalI recognition site (sequence at positions 5 to 10 in SEQ ID NO:29). PT5 and PT3 contain the 5'- and 3'-terminal nucleotide sequences of the terminator region respectively, and the 5'-terminal of PT5 has restriction enzymes SalI and PstI recognition sites (sequence of positions 1 to 12 in SEQ ID NO:30), and the 5'-terminal of PT3 has restriction enzymes HindIII and PstI recognition sites (sequence at positions 1 to 12 in SEQ ID NO:31).

Plasmid pAc1-7 containing the actin gene was mixed with primers PP5 and PP3 and the mixture was subjected to PCR (30 seconds at 94° C., 1 minute at 55° C., and 1 minute at 72° C.)×25 cycles) using rTaq polymerase (Takara Shuzo Co., Ltd.).

The reaction product was subjected to agarose gel electrophoresis, and the amplified DNA fragment was recovered. The recovered DNA fragment was ligated to vector pT7 Blue T-Vector (Novagene) to construct pAcP containing the actin gene promoter region (FIG. 6). Similarly, pAcT containing the actin gene terminator region was constructed by PCR using PT5 and PT3 ((30 seconds at 94° C., 1 minute at 45° C., and 1 minute at 72° C.)×25 cycles) (FIG. 6).

Using a dye primer cycle sequencing kit and a dye terminator cycle sequencing kit (Perkin-Elmer) with above plasmids as templates, the nucleotide sequence was determined, and it was confirmed that the promoter/terminator region was accurately amplified.

(3-2-2) Construction of Expression Cassette

Plasmid pAcP was cleaved with EcoRI and SalI and separated by agarose gel electrophoresis to give the 1.0 kb actin gene promoter region. In the same manner, plasmid pAcT was cleaved with SalI and HindIII to separate the 0.5 kb actin gene terminator region. The 2 kinds of DNA fragment were inserted into the EcoRI-HindIII site in pUC118 to construct pMAc (FIG. 6).

Plasmid pMAc has the actin gene promoter and terminator region between the EcoRI-HindIII sites in pUC118, and various structural genes can be introduced into the SalI and PstI sites between the promoter and terminator.

(3-2-3) Construction of Expression Plasmid for G418 Resistance Gene

An expression plasmid having the G418 resistance gene inserted into the site between the actin gene promoter and terminator was constructed. The G418 resistance gene derived from transposon Tn5 was obtained from plasmid pNEO (Pharmacia) by the PCR technique. The following 2 primers were synthesized according to a report of Jorgensen et al. (Jorgensen, R. A. et al., Mol. Gen. Genet. 177, 65 (1979)):

| PGR5: | SEQ ID NO:32 |
| PGR3: | SEQ ID NO:33 |

These primers were mixed with pNEO and the mixture was subjected to PCR ((30 seconds at 94° C., 1 minute at 55° C., and 1 minute at 72° C.)×25 cycles) using rTaq polymerase.

Figure 7:
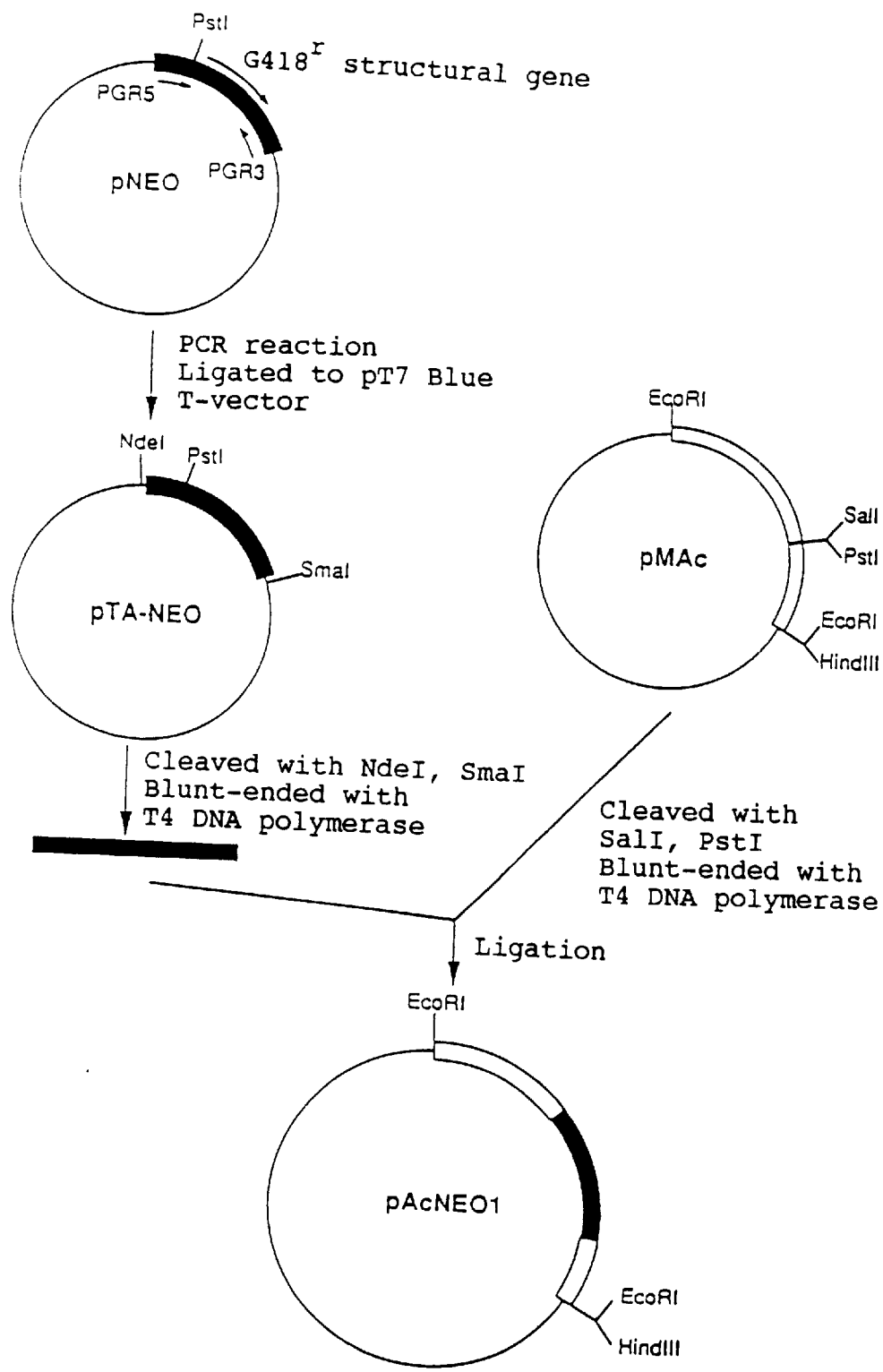
FIG. 7 shows a scheme for constructing a G418 resistance gene expression plasmid pAcNEO1 using the actin gene promoter and terminator.

The reaction product was subjected to agarose gel electrophoresis and the amplified DNA fragment was recovered. The recovered DNA fragment was ligated to vector pT7 Blue T-Vector to construct plasmid pTA-NEO (FIG. 7). Plasmid pTA-NEO was cleaved with NdeI and SmaI and blunt-ended with T4 polymerase, and then the G418 resistance gene fragment was recovered by agarose gel electrophoresis. This G418 resistance gene fragment was ligated to pMAc previously cleaved with SalI and PstI and blunt-ended with T4 DNA polymerase, to construct pAcNEO1 (FIG. 7).

EXAMPLE 4

Expression of a Heterologous Gene by FDH Promoter

In this example, an expression vector for an acid phosphatase gene derived from Saccharomyces cerevisiae was constructed using the promoter and terminator region for formate dehydrogenase (FDH) gene derived from Candida boidinii S2 AOU-1 and then used to transform Candida boidinii.

(4-1) Construction of an Expression Cassette

Figure 8:
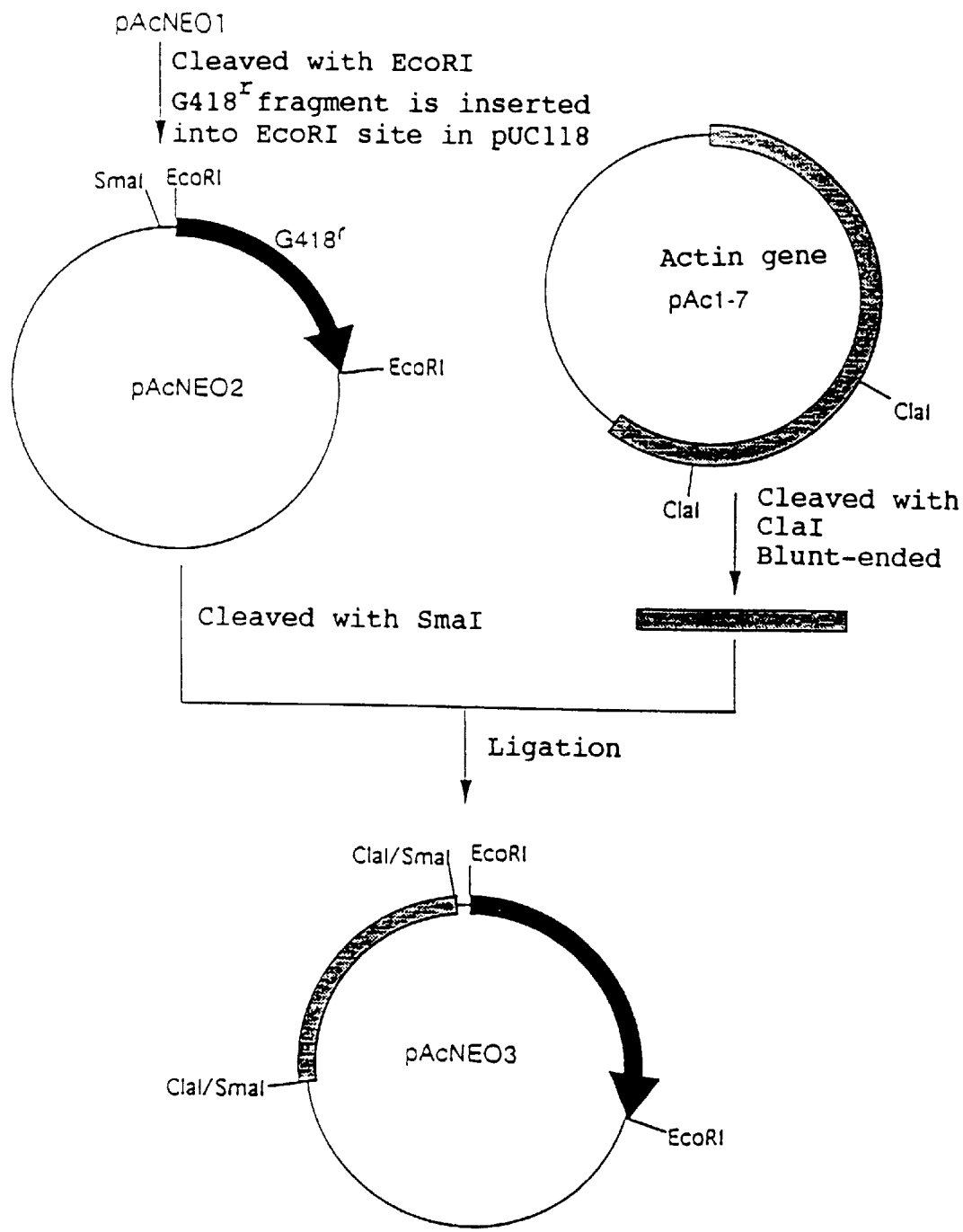
FIG. 8 shows a scheme for constructing plasmids pAcNEO2 and pAcNEO3.

A plasmid for expressing a heterologous gene by the FDH promoter having the G418 resistance gene as a marker gene and the actin gene region as a homologous region was constructed. A DNA fragment containing the G418 resistance gene was separated from pAcNEO1 by cleavage with EcoRI and inserted into the EcoRI site in pUC118 to construct plasmid pAcNEO2 (FIG. 8). By cleavage with ClaI, a 2 kb DNA fragment was separated from plasmid pAc1-7 containing the actin gene, then blunt-ended with T4 polymerase, and inserted into the SmaI site in plasmid pAcNEO2 to construct pAcNEO3 (FIG. 8).

A 2.6 kb DNA fragment containing the FDH promoter and terminator region was separated from pFdhPT and inserted into the SalI-XbaI site in pAcNEO3 to construct pFexAG (FIG. 4).

(4-2) Construction of Acid Phosphatase Expression Plasmid

A plasmid in which the acid phosphatase gene (PHO5 gene) from Saccharomyces cerevisiae had been inserted into the site between the FDH promoter and terminator in the above plasmid pFexAG was constructed.

A PHO5 structural gene was obtained using PCR according to a report of Arima et al. (Arima, K. et al., Nucleic Acids Res., 11, 1657 (1983)). The following 2 oligonucleotides were synthesized as PCR primers:

| PPHO5: | SEQ ID NO:34 |
| PPHO3: | SEQ ID NO:35 |

PPHO5 has a NotI restriction enzyme cleavage site (sequence at positions 1 to 8 in SEQ ID NO:34) before the initiation codon of the PHO5 gene, and PPHO3 has an SmaI restriction enzyme cleavage site (sequence at positions 1 to 6 in SEQ ID NO:35) after the termination codon of the PHO5 gene.

Genomic DNA prepared from Saccharomyces cerevisiae S288C was mixed with primers PHO5 and PPHO3 and the mixture was subjected to PCR ((30 seconds at 94° C., 1 minute at 53° C., and 2 minutes at 72° C.)×25 cycles).

The reaction product was subjected to agarose gel electrophoresis, and the amplified DNA fragment was recovered. The recovered DNA fragment was ligated to vector pT7 Blue T-Vector to construct plasmid pTA-PHO5. Plasmid pTA-PHO5 was cleaved with NotI and SmaI, and a PHO5 gene fragment was recovered. This PHO5 gene fragment was inserted into the NotI-SmaI site in plasmid pFexAG to construct pFPhoAG.

(4-3) Transformation

Candida boidinii ATCC 48180 was transformed with the BglII-cleaved plasmid pFPhoAG to yield transformants with G418 resistance. This transformation was conducted in accordance with a method disclosed in detail by Sakai (Sakai Y. et al., J. Bacteriol., 175, 3556 (1993)).

The transformants were screened in a YPD plate medium containing 0.3 mg/ml G418 in which the host cells could not grow.

(4-4) Confirmation of Expression of the PHO5 Gene

One strain (300-1) among the transformants and the parent strain (ATCC48180) were cultured in a medium containing methanol or glucose as a carbon source, and the amount of the cells and its acid phosphatase activity were determined.

The methanol yeast was cultured in a medium, pH 5.5 containing 1.5% carbon source, 0.67% yeast nitrogen base (Difco) and 0.5% yeast extract (Difco). The measurement of acid phosphatase activity was carried out according to the method of Toh-e et al. (Toh-e, A. et al., J. Bacteriol., 113, 727 (1973)) where a suspension of the washed cells were used as the enzyme. One unit of enzyme activity was assumed to be the amount of the enzyme catalyzing formation of 1 mmole of p-nitrophenol at 30° C. per minute.

As shown in Table 1, no activity could be detected in the parent strain and in the transformant cultured on glucose, while the activity was detected in the transformant cultured on methanol. This indicated that like the formate dehydrogenase gene from *Candida boidinii*, the expression of the PHO5 gene is induced by methanol.

TABLE 1

Acid Phosphatase Activity of the Parent Strain and Transformant

| Strain | Carbon Source | Cell Amount (OD610) | Activity (Unit) in 1 ml Culture |
| --- | --- | --- | --- |
| parent strain | glucose (1.5%, w/v) | 10.7 | not detected |
|  | methanol (1.5%, v/v) | 5.9 | not detected |
| transformant | glucose (1.5%, w/v) | 10.6 | not detected |
|  | methanol (1.5%, v/v) | 5.9 | 0.70 |

The above transformed cells 300-1 were cultured in a medium containing glucose, ethanol, methanol or glycerol as a carbon source, and the amount of the cells and its acid phosphatase activity were determined. As shown in Table 2, the PHO5 gene was induced strongly by methanol only.

TABLE 2

Effect of Carbon Source on Expression of Acid Phosphatase Gene in Transformant

| Carbon Source | Cell Amount (OD610) | Activity (Unit) in 1 ml Culture |
| --- | --- | --- |
| methanol (1.5%, v/v) | 7.7 | 1.05 |
| glucose (1.5%, w/v) | 15.3 | not detected |
| glycerol (1.5%, w/v) | 13.5 | 0.021 |
| ethanol (1.5%, v/v) | 13.4 | 0.014 |

Further, the transformant 300-1 were cultured in a medium containing 0.17% yeast nitrogen base w/o amino acids and ammonium sulfate (Difco) and the various carbon and nitrogen sources shown in Table 3, and then the acid phosphatase activity was determined. The relative acid phosphatase activities of the cells are shown in Table 3 where the specific activity (unit/OD610) of the acid phosphatase cultured on methanol as a carbon source and on ammonium sulfate as a nitrogen source is expressed as 100. The expression of acid phosphatase was induced not only by methanol, but also by formic acid, methylamine, dimethylamine, trimethylamine, or choline. Formic acid, methylamine, dimethylamine, trimethylamine, and choline had an inducible effect even in the presence of glucose in the medium. This indicated that the formate dehydrogenase gene promoter undergoes regulation different from that of the alcohol oxidase gene promoter.

TABLE 3

Effect of Carbon and Nitrogen Sources on Expression of Acid Phosphatase Gene in Transformant

| Medium | PHO5 activity |
| --- | --- |
| methanol (1.5%, v/v) + ammonium sulfate (0.5%, w/v) | 100 |
| glucose (1.5%, w/v) + ammonium sulfate (0.5%, w/v) | not detected |
| glycerol (1.5%, w/v) + ammonium sulfate (0.5%, w/v) | not detected |
| glucose (1.5%, w/v) + sodium formate (0.5%, w/v) + ammonium sulfate (0.5%, w/v) | 8.7 |
| glycerol (1.5%, w/v) + sodium formate (0.5%, w/v) + ammonium sulfate (0.5%, w/v) | 21 |
| glucose (1.5%, w/v) + methylamine hydrochloride (0.5%, w/v) | 4.8 |
| glycerol (1.5%, w/v) + methylamine hydrochloride (0.5%, w/v) | 23 |
| glucose (1.5%, w/v) + dimethylamine hydrochloride (0.5%, w/v) | 7.0 |
| glycerol (1.5%, w/v) + dimethylamine hydrochloride (0.5%, w/v) | 29 |
| glucose (1.5%, w/v) + trimethylamine hydrochloride (0.5%, w/v) | 6.5 |
| glycerol (1.5%, w/v) + trimethylamine hydrochloride (0.5%, w/v) | 32 |
| glucose (1.5%, w/v) + choline chloride (0.5%, w/v) | 20 |
| glycerol (1.5%, w/v) + choline chloride (0.5%, w/v) | 49 |

(4-5)

*Candida boidinii* IFO 10035, *Candida boidinii* IFO 10240, and *Candida boidinii* IFO 10574 were transformed respectively with BglII-cleaved plasmid pFPhoAG to yield transformants with G418 resistance. The respective transformants were cultured in a medium containing methanol or glucose as a carbon source and their acid phosphatase activities were determined. Acid phosphatase activity was detected in only the transformants cultured on methanol, similar to the result of Example (4-4). This indicated that the formate dehydrogenase promoter disclosed in the present invention functions in every *Candida boidinii* strain.

EXAMPLE 5

In this example, a region necessary for the functions of the FDH promoter was identified by constructing the *Candida boidinii* FDH promoter from which its upstream region was deleted and then measuring acid phosphatase activity under the control of the 5'-deletion derivatives of FDH promoter.

(5-1) Construction of Expression Plasmid

To construct an expression plasmid containing the promoter derived from *Candida boidinii* S2 AOU-1, a URA3 gene and KST2515 that is a mutant strain on the URA3 gene were obtained from *Candida boidinii* KST25.

The URA3 gene was cleaved with SalI and PstI, and the 2.6 kb SalI-PstI fragment was inserted into pBluescript II SK−. The resulting plasmid was designated pCBU3. Identification of KST25 was based on "Yeasts: Characteristics and Identification" written by Barnett. The URA3 gene and KST2515 were obtained according to a conventional method (Sakai Y. et al., J. Bacteriol., 173, 7458 (1991)). Although *Candida boidinii* KST2515 was used in this example, other *Candida boidinii* strains such as IFO 10035 is easily applicable in a usual manner.

Figure 9:
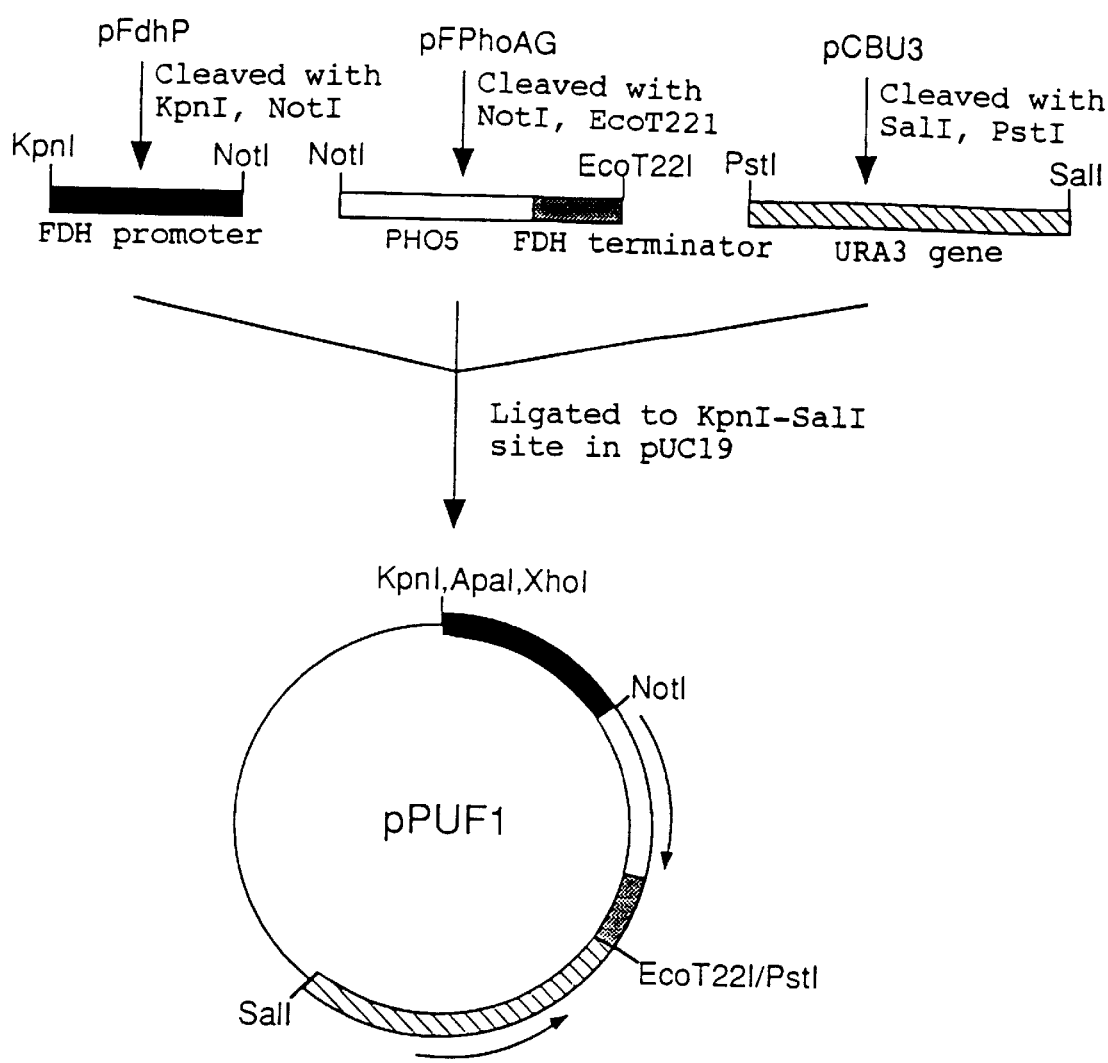
FIG. 9 shows a scheme for constructing plasmid pPUF1.

A 1.5 kb DNA fragment obtained by cleaving plasmid pFdhP with KpnI and NotI, a 2.0 kb DNA fragment obtained by cleaving pFPhoAG with NotI and Eco T22I, and a 2.6 kb DNA fragment obtained by cleaving pCBU3 with SalI and PstI were inserted into the KpnI-SalI site in pUC19, whereby pPUF1 was constructed (FIG. 9). pPUF1 is an expression plasmid of PHO5 under the control of the FDH promoter, carrying the URA3 gene as a marker gene.

(5-2) Construction of PHO5 Expression Plasmid under Control of 5'-Deletion Derivatives of FDH Promoter The FDH promoter from which the upstream region was deleted was constructed by using a deletion kit for kilosequence (Takara Shuzo Co., Ltd.) or PCR. Plasmid pPUF1 was cleaved with ApaI and XhoI and treated with the deletion kit for kilosequence, so that PHO5 expression plasmids under the control of the 5'-deletion derivatives of FDH promoter, i.e. pPUF15, pPUF24, pPUF44, pPUF54, pPUF56, pPUF79, pPUF308, pPUF310 and pPUF320 were obtained. Using a dye primer cycle sequencing kit (Perkin-Elmer) with above plasmids as templates, the nucleotide sequence was determined. As a result, it was confirmed that plasmids pPUF15, pPUF24, pPUF44, pPUF54, pPUF56, pPUF79, pPUF308 and pPUF310 contain FDH promoter regions which are 1215 bp, 1000 bp, 839 bp, 690 bp, 756 bp, 403 bp, 228 bp and 115 bp long respectively.

To prepare by PCR the FDH promoter from which the upstream region was deleted, the following oligonucleotides were synthesized:

| | |
|---|---|
| PF819: | (SEQ ID NO:38) |
| PF801: | (SEQ ID NO:39) |
| PF779: | (SEQ ID NO:40) |
| PF668: | (SEQ ID NO:41) |
| PF642: | (SEQ ID NO:42) |
| PF622: | (SEQ ID NO:43) |
| PF602: | (SEQ ID NO:44) |
| PF194: | (SEQ ID NO:45) |
| PF161: | (SEQ ID NO:46) |
| PRV3: | (SEQ ID NO:47) |

PCR was carried out using the above oligonucleotide PF819, PF801, PF779, PF668, PF642, PF622, PF602, PF194 or PF161 and PRV3 as primers and pPUF1 as a template ((30 minutes at 94° C., 1 minute at 55° C. and 1 minute at 72° C.)×20 cycles).

Each of the amplified DNA fragments was cloned in pT7 Blue T-Vector, then cut off with XhoI and NotI, and inserted into the XhoI-NotI site in pPUF1. PHO5 expression plasmid containing a 819 bp promoter region obtained from primer PF819 was designated pPUF819, PHO5 expression plasmid containing a 801 bp promoter region obtained from primer PF801 was designated pPUF801, PHO5 expression plasmid containing a 779 bp promoter region obtained from primer PF779 was designated pPUF779, PHO5 expression plasmid containing a 668 bp promoter region obtained from primer PF668 was designated pPUF668, PHO5 expression plasmid containing a 642 bp promoter region obtained from primer PF642 was designated pPUF642, PHO5 expression plasmid containing a 622 bp promoter region obtained from primer PF622 was designated pPUF622, PHO5 expression plasmid containing a 602 bp promoter region obtained from primer PF602 was designated pPUF602, PHO5 expression plasmid containing a 194 bp promoter region obtained from primer PF194 was designated pPUF194, and PHO5 expression plasmid containing a 161 bp promoter region obtained from primer PF161 was designated pPUF161.

(5-3) Transformation

5 μg of each plasmid DNA obtained in Example (5-2) was cleaved with BamHI and transformed into *Candida boidinii* KST2515. For each plasmid, some colonies were picked up from the resulting transformants and cultured in a medium, pH 5.5 containing 1.5% methanol, 0.67% yeast nitrogen base and 0.5% yeast extract (referred to hereinafter as "ME medium") or in a medium, pH 5.5 containing 1.0% glucose, 0.5% sodium formate and 0.67% yeast nitrogen base (referred to hereinafter as "GF medium"), and acid phosphatase activity was determined.

According to a prior literature (Sakai Y. et al., J. Bacteriol., 173, 7458 (1991)), about half the transformants in transformation with URA3 as a marker have one copy of a plasmid integrated into the chromosomal DNA, and thus the largest distribution value of the acid phosphatase activity of the cells transformed with each plasmid was assumed to be the acid phosphatase activity of the transformed cells with one copy integrated into the chromosomal DNA. It was confirmed by Southern analysis that one copy of a plasmid had actually been integrated into a chromosomal DNA. In FIG. 10, the activities (unit/OD610) of the acid phosphatase of the transformants with the respective plasmids are shown as relative values to the specific activity (as 100) of the acid phosphatase of the transformant transformed with pPUF1. The results in FIG. 10 revealed that 194 bp (e.g. the nucleotide sequence of SEQ ID NO:48) or more, preferably 839 bp (e.g. the nucleotide sequence of SEQ ID NO:50) or more of the promoter region is required for induction by methanol, and that 194 bp (e.g. the nucleotide sequence of SEQ ID NO:48) or more, preferably 642 bp (e.g. the nucleotide sequence of SEQ ID NO:49) or more of the promoter region is required for induction by formic acid.

INDUSTRIAL APPLICABILITY

According to the present invention, there are provided a promoter and/or a terminator having a strong transcriptional activity to express a heterologous gene. A highly expressed heterologous gene product can be obtained by culturing a transformant transformed with an expression vector containing the promoter, the terminator and a desired heterologous gene.

What is claimed is:

1. A promoter for a formate dehydrogenase gene from *Candida boidinii*, which comprises the nucleotide sequence of SEQ ID NO:48.

2. A promoter for a formate dehydrogenase gene from *Candida boidinii*, which comprises a nucleotide sequence selected from the group consisting of SEQ ID NO: 1, 49 and 50.

3. A terminator for a formate dehydrogenase gene from *Candida boidinii*, which comprises the nucleotide sequence of SEQ ID NO:2.

4. A gene expression cassette comprising the promoter of claim 1 or claim 2, a heterologous gene and a terminator for a formate dehydrogenase gene from *Candida boidinii*, which comprises the nucleotide sequence of SEQ ID NO:2.

5. The gene expression cassette according to claim 4, wherein the heterologous gene is an acid phosphatase gene.

6. A recombinant expression vector comprising the gene expression cassette of claim 4.

7. A transformant transformed with the recombinant expression vector of claim 6.

8. A process for producing an expression product of a heterologous gene, which comprises culturing the transformant of claim 7 and recovering an expression product of a heterologous gene from the culture.

9. The process for producing an expression product according to claim 8, wherein the expression product of a heterologous gene is acid phosphatase.

10. The process for producing an expression product according to claim 8, wherein the medium contains at least one compound having an oxygen or nitrogen atom having at least one C1 substituent group bound to the atom.

11. The process for producing an expression product according to claim 10, wherein the compound having an oxygen atom is methanol or formic acid or salts thereof.

12. The process for producing an expression product according to claim 10, wherein the compound having a nitrogen atom is at least one member selected from the group consisting of methylamine, dimethylamine, trimethylamine and a N-substituted-methyl-containing ammonium compound.

13. The process for producing an expression product according to claim 12, wherein the N-substituted-methyl-containing ammonium compound is choline.

14. A recombinant expression vector comprising the gene expression cassette of claim 5.

15. The process for producing an expression product according to claim 9, wherein the medium contains at least one compound having an oxygen or nitrogen atom wherein the oxygen or nitrogen atom has at least one C1 substituent group.

* * * * *

SEQUENCE LISTING (1) GENERAL INFORMATION:

(iii) NUMBER OF SEQUENCES: 51

(2) INFORMATION FOR SEQ ID NO:1:

(i) SEQUENCE CHARACTERISTICS:
      (A) LENGTH: 1478 base pairs (B) TYPE: nucleic acid
    (C) STRANDEDNESS: double
    (D) TOPOLOGY: linear (ii) MOLECULE TYPE: DNA (genomic)

(vi) ORIGINAL SOURCE:
    (A) ORGANISM: Candida boidinii (xi) SEQUENCE DESCRIPTION: SEQ ID NO:1:

```
GTCAACAAAT CAATCAGCCA ATCTACCAAT CAATTAAAAA TACACTGAAG TGATATAGTT      60

TAGTCTAATC AAAGTTGAAT AACCCCAGAC ATGGTTGAAA TCTTAGAAGC CACAAATATC     120

AACAGGCCAA ATCGGCTCTC GGAGAATCTT TTCTGGCTTC CAGTGTATGG GCTGTTACGC     180

TACACTCAGT AAACTGCCTC CTCTCTGCAT CTCCATCTTC CCCACATTTT ATGCACTAAA     240

CGCCATCGCA ATATTTCACT AGACTTACAG AACCTTTCAC AATATTAACT CTCTGTCTCT     300

GATGTAATCG ATACAATTCA ATTCAACTAA ATACCATGAT AAACTCAAAT AATTGAAGGA     360

CTCCGATTTA TGCTTATCCA ACACTTATAT CCACTTGTAT TCATTACCGT GCTGTCTTCC     420

GTGGATCAGA TTGCCTCTGT CTCCCTATTC GTCAAATGGC AGAGCAATCA GGGAAAAAGC     480

TGGGTTTTTA CTGAATTCAG TCAAGTAATC CTGTCGGACT TTTTAATATC TAGCTTTCAC     540

AAAAACCAAC AACAACAACC GCTAATCCCA TCAAACAATT AAACAATTGT TACAATTGTC     600

ACAATTCTTG GATATACAAT AATTAAACAT ACGTACATTC TTACATACAT ATAGAGTTTG     660

AAATAGATAC ATTACCCAGT GTCATCGATA TTATGCCCCG CCTTTTTCAC TTGAAACAAT     720

AACTATTATT ACTACTATTA TTATTTCTAT TCATATATCC TAAAAATTAT ATTAAAATTG     780

GCTCTTTTAT GCAAAAAATG TACATTTATG GTAATACTAG TCAGATGTTA TAATTATATC     840

TTTACCACTA TCCAATTAAA ATCCATGGAT CAGACGGTAG TTTTTATATC TGTAACATCT     900

TACTACTACC ACTACTACTA CCACTACTAC TACCACTACT ACTACTACTGA             960

TAATAAGGTA TACTACATTT TATCATACGT GAAATGTAAC GCGTAGATTA AACATTTTTT    1020

TAAAATTACT GATCAGTACT TTCCACAATA AGCACTTATT AATATGTGCC TCTTTAAAAT    1080

TACTTAATTC CCTTTACTTT TCATTTTTAC AACCGCTTTG GTATTTACCC CCAGAGTGTT    1140

TTAATTGCAA TTGAATTCTT ATTTTAATTT CCATTACTTT CTTTGTACCA TAATGAAATT    1200

GCCGAGTTGT CCCTCCTTTG AATTTAAATC ATTCTCTAAT ATTTAACTTT AATTTTAATA    1260

TTTTAGTTAT TTATTTGAAT TAAAGTAAAT TCAACTAAAA ATTGAACTAT TTAAACACTA    1320

TGATTTCCTT CAATTATATT AAAATCAATT TCATATTTCC TTACTTCTTT TTGCTTTATT    1380

ATACATCAAT AACTCAATTA ACTCATTGAT TATTTGAAAA AAAAAAACAT TTATTAACTT    1440

AACTCCCCGA TTATATATTA TATTATTGAC TTTACAAA                             1478
```

(2) INFORMATION FOR SEQ ID NO:2:

(i) SEQUENCE CHARACTERISTICS:
        (A) LENGTH: 989 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Candida boidinii (xi) SEQUENCE DESCRIPTION: SEQ ID NO:2:

```
ATTTTCTTAA CTTGAAAACT ATAATTGCTA TAACAATTCT TCAATTTCTC TTTTTCTTCC      60

TTTTTTTGAA GAATTTTTAA CAATCAAAAT TTTGACTCTT TGATTTCCCG CAATCTCTGA     120
```

```
GCTCAGCATA CTCATTATTA TTTTATTATT ATTATTATTA TTACTTTTAT TATTATTATA      180

TTTTTTCTTC TTTAACGATA TCGTTTGTGT TTTATCTTTT ATGATTTAAA TTTTATACGA      240

ATTTATGAAT ACAACAAAAT ATTTAAGTTT ACACAATGTA GTAAATTAAA AGTTAATCAG      300

TAAAATGTAT TGTAAGTTAC ATATATCATA TATCAGTGTC TTGATATATA TAAAGAAAAC      360

GTTGCTTATG TAATCAGGCA CACGTTGACA GCGTGGTGCC CTGAACAGCA ACCGCAATTT      420

TGACCACGCA CGGGCGGTCT TATCTCCAGC CGGCTGCTTT CAGTCTCCAA GCGATAAGGC      480

CACAATAGCA ATGGCAATCA CAGCCACAGC CACGCCAGCC ATCTACTTAC GCTCTCTCTT      540

CCTGCTGAGG CTATCGGTAC TCGCACTACT ATTAGCCCTT CCCTATTCTT CCTCTTATCA      600

GCTTCATCTC TTGAGTCTTA CCCCATGCAT TCATCCTATC CTATCCTTCG ATTGCCACCT      660

CTCATCTCAT CTGCCGTTCT TGACTGTCAA TCTATCCAAA ATAGACGACT AACGGAGTTG      720

GTGGTTTAAT TTATGGATAC CATATAGTTC ATACCATTGA ATCACCACCA CCACCATCAA      780

TGTCTCTTTG TTACAATCGT ATATTACAAT TAACTCTTTG TGGCTTGAAA TGTGTATTGT      840

ATGCACTCTG ATTTCTAGTT CCTCTGTTTC CTTGCTAATT CTAAATTGAC CAAACCCTTG      900

AACTGTCTTG ACTTTATATC ATTTTAGTTC AATTAAATTC AATTAAATTA AATTCAATTC      960

AATTCAATTT TTCTTTAAAA CAATCTAGA                                        989

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Met Lys Ile Val Leu Val Leu Tyr Asp Ala Gly Lys His Ala Ala Asp
1               5                   10                  15

Glu Glu Lys Leu
            20

(2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Lys Leu Tyr Gly Cys Thr Glu Asn Lys
1               5

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Lys Glu Leu Leu Ser Lys
```

```
1               5

(2) INFORMATION FOR SEQ ID NO:6:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Lys Asp His Pro Trp Arg Asp Met Arg Asn Lys
1               5                   10

(2) INFORMATION FOR SEQ ID NO:7:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Lys Asp Gln Gly His Glu Leu Ile Thr Thr Ser
1               5                   10

(2) INFORMATION FOR SEQ ID NO:8:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Lys Tyr Gly Ala Gly Asn Ala Met Thr Pro His Tyr Ser Gly Thr Thr
1               5                   10                  15

Leu Asp Ala Gln Thr Arg Tyr Ala Glu Gly
                20                  25

(2) INFORMATION FOR SEQ ID NO:9:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Lys Glu Leu Leu Tyr Tyr Asp Tyr Gln Ala Leu Pro Lys
1               5                   10

(2) INFORMATION FOR SEQ ID NO:10:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide
```

(xi) SEQUENCE DESCRIPTION: SEQ ID NO:10:

Lys Leu Val Val Val Ala Gly Val Gly Ser Asp His Ile Asp Leu Asp
1               5                   10                  15

Tyr Ile (2) INFORMATION FOR SEQ ID NO:11:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:11:

Lys Ile Val Leu Val Leu Tyr Asp Ala Gly Lys
1               5                   10

(2) INFORMATION FOR SEQ ID NO:12:

(i) SEQUENCE CHARACTERISTICS:
            (A) LENGTH: 19 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:12:

Lys Phe Asp Tyr Arg Pro Gln Asp Ile Ile Leu Leu Asn Gly Glu Tyr
1               5                   10                  15

Val Thr Lys (2) INFORMATION FOR SEQ ID NO:13:

(i) SEQUENCE CHARACTERISTICS:
            (A) LENGTH: 21 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:13:

Lys His Ile Pro Asp Ala Asp Ile Ile Ile Thr Thr Pro Phe His Pro
1               5                   10                  15

Ala Tyr Ile Thr Lys
            20

(2) INFORMATION FOR SEQ ID NO:14:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:14:

Lys Leu Gly Ile Ala Asn Trp Leu Lys
1               5

(2) INFORMATION FOR SEQ ID NO:15:

(i) SEQUENCE CHARACTERISTICS:

(A) LENGTH: 31 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:15:

Lys Val Gly Ala Arg Arg Val Glu Asn Ile Glu Glu Leu Val Ala Gln
1               5                   10                  15

Ala Asp Ile Val Thr Val Asn Ala Pro Leu His Ala Gly Thr Lys
                20                  25                  30

(2) INFORMATION FOR SEQ ID NO:16:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:16:

Lys Asn Ile Leu Glu Ser Phe Phe Thr Gly Lys
1               5                   10

(2) INFORMATION FOR SEQ ID NO:17:

(i) SEQUENCE CHARACTERISTICS:
            (A) LENGTH: 31 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:17:

CGCGGATCCT AYGATGCWGG WAARCAYGCW G                                  31

(2) INFORMATION FOR SEQ ID NO:18:

(i) SEQUENCE CHARACTERISTICS:
            (A) LENGTH: 32 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:18:

CGCGGATCCT ARTGWGGWGT CATWGCRTTW CC                                 32

(2) INFORMATION FOR SEQ ID NO:19:

(i) SEQUENCE CHARACTERISTICS:
            (A) LENGTH: 3562 base pairs
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (A) ORGANISM: Candida boidinii (xi) SEQUENCE DESCRIPTION: SEQ ID NO:19:

GTCAACAAAT CAATCAGCCA ATCTACCAAT CAATTAAAAA TACACTGAAG TGATATAGTT    60

```
TAGTCTAATC AAAGTTGAAT AACCCCAGAC ATGGTTGAAA TCTTAGAAGC CACAAATATC    120

AACAGGCCAA ATCGGCTCTC GGAGAATCTT TTCTGGCTTC CAGTGTATGG GCTGTTACGC    180

TACACTCAGT AAACTGCCTC CTCTCTGCAT CTCCATCTTC CCCACATTTT ATGCACTAAA    240

CGCCATCGCA ATATTTCACT AGACTTACAG AACCTTTCAC AATATTAACT CTCTGTCTCT    300

GATGTAATCG ATACAATTCA ATTCAACTAA ATACCATGAT AAACTCAAAT AATTGAAGGA    360

CTCCGATTTA TGCTTATCCA ACACTTATAT CCACTTGTAT TCATTACCGT GCTGTCTTCC    420

GTGGATCAGA TTGCCTCTGT CTCCCTATTC GTCAAATGGC AGAGCAATCA GGGAAAAAGC    480

TGGGTTTTTA CTGAATTCAG TCAAGTAATC CTGTCGGACT TTTTAATATC TAGCTTTCAC    540

AAAAACCAAC AACAACAACC GCTAATCCCA TCAAACAATT AAACAATTGT TACAATTGTC    600

ACAATTCTTG GATATACAAT AATTAAACAT ACGTACATTC TTACATACAT ATAGAGTTTG    660

AAATAGATAC ATTACCCAGT GTCATCGATA TTATGCCCCG CCTTTTTCAC TTGAAACAAT    720

AACTATTATT ACTACTATTA TTATTTCTAT TCATATATCC TAAAAATTAT ATTAAAATTG    780

GCTCTTTTAT GCAAAAAATG TACATTTATG GTAATACTAG TCAGATGTTA TAATTATATC    840

TTTACCACTA TCCAATTAAA ATCCATGGAT CAGACGGTAG TTTTTATATC TGTAACATCT    900

TACTACTACC ACTACTACTA CCACTACTAC TACCACTACT ACTACCACTA CTACTACTGA    960

TAATAAGGTA TACTACATTT TATCATACGT GAAATGTAAC GCGTAGATTA AACATTTTTT   1020

TAAAATTACT GATCAGTACT TTCCACAATA AGCACTTATT AATATGTGCC TCTTTAAAAT   1080

TACTTAATTC CCTTTACTTT TCATTTTTAC AACCGCTTTG GTATTTACCC CCAGAGTGTT   1140

TTAATTGCAA TTGAATTCTT ATTTTAATTT CCATTACTTT CTTTGTACCA TAATGAAATT   1200

GCCGAGTTGT CCCTCCTTTG AATTTAAATC ATTCTCTAAT ATTTAACTTT AATTTTAATA   1260

TTTTAGTTAT TTATTTGAAT TAAAGTAAAT TCAACTAAAA ATTGAACTAT TTAAACACTA   1320

TGATTTCCTT CAATTATATT AAAATCAATT TCATATTTCC TTACTTCTTT TTGCTTTATT   1380

ATACATCAAT AACTCAATTA ACTCATTGAT TATTTGAAAA AAAAAAACAT TTATTAACTT   1440

AACTCCCCGA TTATATATTA TATTATTGAC TTTACAAAAT GAAGATCGTT TTAGTCTTAT   1500

ATGATGCTGG TAAGCACGCT GCTGATGAAG AAAAATTATA TGGTTGTACT GAAAATAAAT   1560

TAGGTATTGC TAATTGGTTA AAAGATCAAG GTCATGAACT AATTACTACT TCTGATAAAG   1620

AAGGTGAAAC AAGTGAATTG GATAAACATA TCCCAGATGC TGATATTATC ATCACCACTC   1680

CTTTCCATCC TGCTTATATC ACTAAGGAAA GACTTGACAA GGCTAAGAAC TTAAAATTAG   1740

TCGTTGTCGC TGGTGTTGGT TCTGATCACA TTGATTTAGA TTATATTAAT CAAACAGGTA   1800

AGAAAATCTC AGTCTTGGAA GTTACAGGTT CTAATGTTGT CTCTGTTGCT GAACACGTTG   1860

TCATGACCAT GCTTGTCTTG GTTAGAAATT TCGTTCCAGC ACATGAACAA ATTATTAACC   1920

ACGATTGGGA GGTTGCTGCT ATCGCTAAGG ATGCTTACGA TATCGAAGGT AAAACTATTG   1980

CTACCATTGG TGCTGGTAGA ATTGGTTACA GAGTCTTGGA AAGATTACTC CCTTTTAATC   2040

CAAAGAATT ATTATACTAC GATTATCAAG CTTTACCAAA AGAAGCTGAA GAAAAAGTTG   2100

GTGCTAGAAG AGTTGAAAAT ATTGAAGAAT TAGTTGCTCA AGCTGATATC GTTACAGTTA   2160

ATGCTCCATT ACACGCAGGT ACAAAAGGTT TAATTAATAA GGAATTATTA TCTAAATTTA   2220

AAAAAGGTGC TTGGTTAGTC AATACCGCAA GAGGTGCTAT TTGTGTTGCT GAAGATGTTG   2280

CAGCAGCTTT AGAATCTGGT CAATTAAGAG GTTACGGTGG TGATGTTTGG TTCCCACAAC   2340

CAGCTCCAAA GGATCACCCA TGGAGAGATA TGAGAAATAA ATATGGTGCT GGTAATGCCA   2400

TGACTCCTCA CTACTCTGGT ACTACTTTAG ATGCTCAAAC AAGATACGCT GAAGGTACTA   2460
```

-continued

```
AAAATATCTT GGAATCATTC TTTACTGGTA AATTTGATTA CAGACCACAA GATATTATCT    2520

TATTAAATGG TGAATACGTT ACTAAAGCTT ACGGTAAACA CGATAAGAAA TAAATTTTCT    2580

TAACTTGAAA ACTATAATTG CTATAACAAT TCTTCAATTT CTCTTTTTCT TCCTTTTTTT    2640

GAAGAATTTT TAACAATCAA AATTTTGACT CTTTGATTTC CCGCAATCTC TGAGCTCAGC    2700

ATACTCATTA TTATTTTATT ATTATTATTA TTATTACTTT TATTATTATT ATATTTTTC    2760

TTCTTTAACG ATATCGTTTG TGTTTATCT TTTATGATTT AAATTTTATA CGAATTTATG    2820

AATACAACAA AATATTTAAG TTTACACAAT GTAGTAAATT AAAAGTTAAT CAGTAAAATG    2880

TATTGTAAGT TACATATATC ATATATCAGT GTCTTGATAT ATATAAAGAA AACGTTGCTT    2940

ATGTAATCAG GCACACGTTG ACAGCGTGGT GCCCTGAACA GCAACCGCAA TTTTGACCAC    3000

GCACGGGCGG TCTTATCTCC AGCCGGCTGC TTTCAGTCTC CAAGCGATAA GGCCACAATA    3060

GCAATGGCAA TCACAGCCAC AGCCACGCCA GCCATCTACT TACGCTCTCT CTTCCTGCTG    3120

AGGCTATCGG TACTCGCACT ACTATTAGCC CTTCCCTATT CTTCCTCTTA TCAGCTTCAT    3180

CTCTTGAGTC TTACCCCATG CATTCATCCT ATCCTATCCT TCGATTGCCA CCTCTCATCT    3240

CATCTGCCGT TCTTGACTGT CAATCTATCC AAAATAGACG ACTAACGGAG TTGGTGGTTT    3300

AATTTATGGA TACCATATAG TTCATACCAT TGAATCACCA CCACCACCAT CAATGTCTCT    3360

TTGTTACAAT CGTATATTAC AATTAACTCT TTGTGGCTTG AAATGTGTAT TGTATGCACT    3420

CTGATTTCTA GTTCCTCTGT TTCCTTGCTA ATTCTAAATT GACCAAACCC TTGAACTGTC    3480

TTGACTTTAT ATCATTTTAG TTCAATTAAA TTCAATTAAA TTAAATTCAA TTCAATTCAA    3540

TTTTTCTTTA AACAATCTA GA                                              3562
```

(2) INFORMATION FOR SEQ ID NO:20:

(i) SEQUENCE CHARACTERISTICS:
        (A) LENGTH: 1095 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Candida boidinii (ix) FEATURE:
        (A) NAME/KEY: CDS
        (B) LOCATION: 1..1092

(xi) SEQUENCE DESCRIPTION: SEQ ID NO:20:

```
ATG AAG ATC GTT TTA GTC TTA TAT GAT GCT GGT AAG CAC GCT GCT GAT        48
Met Lys Ile Val Leu Val Leu Tyr Asp Ala Gly Lys His Ala Ala Asp
 1               5                  10                  15

GAA GAA AAA TTA TAT GGT TGT ACT GAA AAT AAA TTA GGT ATT GCT AAT        96
Glu Glu Lys Leu Tyr Gly Cys Thr Glu Asn Lys Leu Gly Ile Ala Asn
            20                  25                  30

TGG TTA AAA GAT CAA GGT CAT GAA CTA ATT ACT ACT TCT GAT AAA GAA       144
Trp Leu Lys Asp Gln Gly His Glu Leu Ile Thr Thr Ser Asp Lys Glu
         35                  40                  45

GGT GAA ACA AGT GAA TTG GAT AAA CAT ATC CCA GAT GCT GAT ATT ATC       192
Gly Glu Thr Ser Glu Leu Asp Lys His Ile Pro Asp Ala Asp Ile Ile
     50                  55                  60

ATC ACC ACT CCT TTC CAT CCT GCT TAT ATC ACT AAG GAA AGA CTT GAC       240
Ile Thr Thr Pro Phe His Pro Ala Tyr Ile Thr Lys Glu Arg Leu Asp
 65                  70                  75                  80

AAG GCT AAG AAC TTA AAA TTA GTC GTT GTC GCT GGT GTT GGT TCT GAT       288
```

| | | | | | | | | | | | | |
|---|---|---|---|---|---|---|---|---|---|---|---|---|
|Lys|Ala|Lys|Asn|Leu|Lys|Leu|Val|Val|Val|Ala|Gly|Val|Gly|Ser|Asp|
| | | |85| | | |90| | | |95| |

```
CAC ATT GAT TTA GAT TAT ATT AAT CAA ACA GGT AAG AAA ATC TCA GTC        336
His Ile Asp Leu Asp Tyr Ile Asn Gln Thr Gly Lys Lys Ile Ser Val
            100                 105                 110

TTG GAA GTT ACA GGT TCT AAT GTT GTC TCT GTT GCT GAA CAC GTT GTC        384
Leu Glu Val Thr Gly Ser Asn Val Val Ser Val Ala Glu His Val Val
        115                 120                 125

ATG ACC ATG CTT GTC TTG GTT AGA AAT TTC GTT CCA GCA CAT GAA CAA        432
Met Thr Met Leu Val Leu Val Arg Asn Phe Val Pro Ala His Glu Gln
    130                 135                 140

ATT ATT AAC CAC GAT TGG GAG GTT GCT GCT ATC GCT AAG GAT GCT TAC        480
Ile Ile Asn His Asp Trp Glu Val Ala Ala Ile Ala Lys Asp Ala Tyr
145                 150                 155                 160

GAT ATC GAA GGT AAA ACT ATT GCT ACC ATT GGT GCT GGT AGA ATT GGT        528
Asp Ile Glu Gly Lys Thr Ile Ala Thr Ile Gly Ala Gly Arg Ile Gly
                165                 170                 175

TAC AGA GTC TTG GAA AGA TTA CTC CCT TTT AAT CCA AAA GAA TTA TTA        576
Tyr Arg Val Leu Glu Arg Leu Leu Pro Phe Asn Pro Lys Glu Leu Leu
            180                 185                 190

TAC TAC GAT TAT CAA GCT TTA CCA AAA GAA GCT GAA GAA AAA GTT GGT        624
Tyr Tyr Asp Tyr Gln Ala Leu Pro Lys Glu Ala Glu Glu Lys Val Gly
        195                 200                 205

GCT AGA AGA GTT GAA AAT ATT GAA GAA TTA GTT GCT CAA GCT GAT ATC        672
Ala Arg Arg Val Glu Asn Ile Glu Glu Leu Val Ala Gln Ala Asp Ile
    210                 215                 220

GTT ACA GTT AAT GCT CCA TTA CAC GCA GGT ACA AAA GGT TTA ATT AAT        720
Val Thr Val Asn Ala Pro Leu His Ala Gly Thr Lys Gly Leu Ile Asn
225                 230                 235                 240

AAG GAA TTA TTA TCT AAA TTT AAA AAA GGT GCT TGG TTA GTC AAT ACC        768
Lys Glu Leu Leu Ser Lys Phe Lys Lys Gly Ala Trp Leu Val Asn Thr
                245                 250                 255

GCA AGA GGT GCT ATT TGT GTT GCT GAA GAT GTT GCA GCA GCT TTA GAA        816
Ala Arg Gly Ala Ile Cys Val Ala Glu Asp Val Ala Ala Ala Leu Glu
            260                 265                 270

TCT GGT CAA TTA AGA GGT TAC GGT GGT GAT GTT TGG TTC CCA CAA CCA        864
Ser Gly Gln Leu Arg Gly Tyr Gly Gly Asp Val Trp Phe Pro Gln Pro
        275                 280                 285

GCT CCA AAG GAT CAC CCA TGG AGA GAT ATG AGA AAT AAA TAT GGT GCT        912
Ala Pro Lys Asp His Pro Trp Arg Asp Met Arg Asn Lys Tyr Gly Ala
    290                 295                 300

GGT AAT GCC ATG ACT CCT CAC TAC TCT GGT ACT ACT TTA GAT GCT CAA        960
Gly Asn Ala Met Thr Pro His Tyr Ser Gly Thr Thr Leu Asp Ala Gln
305                 310                 315                 320

ACA AGA TAC GCT GAA GGT ACT AAA AAT ATC TTG GAA TCA TTC TTT ACT       1008
Thr Arg Tyr Ala Glu Gly Thr Lys Asn Ile Leu Glu Ser Phe Phe Thr
                325                 330                 335

GGT AAA TTT GAT TAC AGA CCA CAA GAT ATT ATC TTA TTA AAT GGT GAA       1056
Gly Lys Phe Asp Tyr Arg Pro Gln Asp Ile Ile Leu Leu Asn Gly Glu
            340                 345                 350

TAC GTT ACT AAA GCT TAC GGT AAA CAC GAT AAG AAA TAA                   1095
Tyr Val Thr Lys Ala Tyr Gly Lys His Asp Lys Lys
        355                 360
```

(2) INFORMATION FOR SEQ ID NO:21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear

```
    (ii) MOLECULE TYPE: other nucleic acid
         (A) DESCRIPTION: /desc = "synthetic DNA"

(xi) SEQUENCE DESCRIPTION: SEQ ID NO:21:

TAAGGTATAC TACATTTTAT CATAC                                              25

(2) INFORMATION FOR SEQ ID NO:22:

(i) SEQUENCE CHARACTERISTICS:
         (A) LENGTH: 38 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "synthetic DNA"

(xi) SEQUENCE DESCRIPTION: SEQ ID NO:22:

GCGGCCGCTT TGTAAAGTCA ATAATATAAT ATATAATC                                 38

(2) INFORMATION FOR SEQ ID NO:23:

(i) SEQUENCE CHARACTERISTICS:
         (A) LENGTH: 41 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "synthetic DNA"

(xi) SEQUENCE DESCRIPTION: SEQ ID NO:23:

GCGGCCGCCC CGGGATTTTC TTAACTTGAA AACTATAATT G                             41

(2) INFORMATION FOR SEQ ID NO:24:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "synthetic DNA"

(xi) SEQUENCE DESCRIPTION: SEQ ID NO:24:

AATGAGTATG CTGAGCTCAG AGATTG                                             26

(2) INFORMATION FOR SEQ ID NO:25:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "synthetic DNA"

(xi) SEQUENCE DESCRIPTION: SEQ ID NO:25:

GAGGTTGCTG CTTTGGTTAT T                                                  21

(2) INFORMATION FOR SEQ ID NO:26:

(i) SEQUENCE CHARACTERISTICS:
         (A) LENGTH: 21 base pairs
         (B) TYPE: nucleic acid
         (C) STRANDEDNESS: single
         (D) TOPOLOGY: linear
```

(ii) MOLECULE TYPE: other nucleic acid
    (A) DESCRIPTION: /desc = "synthetic DNA"

(xi) SEQUENCE DESCRIPTION: SEQ ID NO:26:

GAAACACTTG TGGTGAACGA T                                        21

(2) INFORMATION FOR SEQ ID NO:27:

(i) SEQUENCE CHARACTERISTICS:
        (A) LENGTH: 4818 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Candida boidinii (xi) SEQUENCE DESCRIPTION: SEQ ID NO:27:

| | | | | | |
|---|---|---|---|---|---|
|CATATAACGG|ATCCCACTTA|TATGACTGTA|AGGCAAAGAA|AGGGATTGCA|AAAATTGAAA     60|
|GAATATGATT|CCCATGAATA|CTGGACTGAC|TAAATGTCCT|ATCACGTTGC|CATAAATATC    120|
|ACTCAAGAAT|CACGGTTCGG|TGAAGTTTCC|AAACAATAAA|GAAACCATAT|AGGGTAAAGA    180|
|TAAGAATTTT|AATTTAGTAA|ATGAATTAAA|TTCAGTATGA|TGGCAAGAAA|CACATCATTA    240|
|CACCATATTT|TACTCCTCTA|TTCAGTCTTT|GAGCAGTTTG|GTGTAATATA|ATATTGATGT    300|
|GTTGGCATCT|TTGACTGATT|TCGCATTTGA|TCAATGGCGG|CCCTAAATTC|CGGCGCGATT    360|
|TTTGGTAGAC|GTGCCATGTG|GTCACTGATA|TGTGTAGAGA|GAGATCACTG|ATTGGAGTTT    420|
|GCACATACCA|GGAAATAACC|AGACATTGAA|ATGCCTATCT|ATTCAAAGGG|CGAACAGCTT    480|
|TTAATAAAAT|TCACTTCAAC|ACACTCATTA|ATTACATCAG|CCATTATGTA|TAAATCCTGT    540|
|CTAGGTGTCC|TAAAACATAT|CTTTTTTCTC|TTATCTATAC|AAGGAGTGGC|GCAGGCTTTT    600|
|AGTGAGAGGA|GAGAGTTAAA|ATTAGTTCGA|TGGCTGAGGA|TATTTGAGAG|ATGATCATGG    660|
|CGCAGGCAGG|AACATGGCAG|GCGCAGTCTC|GAGTTGCCAC|CCTCGATTAC|TCAGAGCTTT    720|
|TACATTTACA|GCCATAATGG|GAGGCTCTGA|GGCATATAAT|GTTGCTTCAA|CCCCACGGGT    780|
|TCACACCATG|AACAGTTCTC|TCACCGGGCG|CTTTTTCACC|TGGCTGAAAG|TGCAATTAAA    840|
|TCAAGAGACA|ATAAGAGCAC|GCATCTGATT|TGTAAGAATG|TTACGGATCG|ATTGTTAGTA    900|
|GTACGTAATC|ATAATAGGTA|GTTATGCACT|GCAATCAATA|AGAGTGTGAT|TATATACAAT    960|
|CAGCTGGTGT|TAACTAAATA|TAGTTATGAA|ATTTCACCGC|GCGTTTGGTT|CACGTTTCAG   1020|
|TACCAAGAAT|TGATAATATT|GGCAGCGGTT|CAGTGCGTTT|GCTGCTTCAC|CTCCCGCATT   1080|
|CTCTAGTCCG|GATTCTCTGT|ATTCCCCCTT|ACATTGCTGG|CCATTGCTGG|CCATTCCTGG   1140|
|CAAGGTATAT|GCCACTACTG|TGCCTGATTT|CTTTCACGCC|TGCCTTACCA|TCATGTCTCT   1200|
|TCTGTATATC|CGCCCAACCG|GCAGGACATC|CGCTTACCAC|GCAGCCCACC|GCGTTTATGT   1260|
|GAGCGTCTTG|ACCTCGTCTC|CTTCCCGTTT|GCCCCTGTCA|ACCGCCTCAT|CACTCACCAC   1320|
|AGCCCCTGAA|ATATACACCG|GATCATCCAG|AAATTACGGC|TGACACAGCC|TCTGGATCCC   1380|
|AGGCAGGCAT|TAAGGCATTA|CATCAGATAG|CGACCACCAT|GACTGTACCC|ACTTTAGCCA   1440|
|CTTTAACCAC|TCTGCTACCG|CTCTTCTCTG|TCTTCCAGCT|TGTCGCATTA|GCCTGCGAGT   1500|
|CTTCCCACTG|AGTTCCTTCT|TTCTGTTTCT|GTTTCTCCCA|GTGTCTCCGA|GTTTACCCAC   1560|
|TTGTTTTCAT|TCTCGTTGTT|GTCTCTTGTT|TGTTCAATTA|CCACTCCCAC|CCATTTTCTC   1620|
|TCATTTTCTC|TCTATTCTTT|CCTCCCAGAT|TCTGTATCCG|CCATTTCATT|CATCATTCAT   1680|
|TCACTTATTC|ATCCTTCATC|ATCCATTCAT|TCATTCATTT|ACCCAATTAA|CCTTCCAATC   1740|

```
TATCAATTCA TTAATCAATC AACGCCTTTC CCTCCGAACA CTTCACTCAA TTCCTCTTCT    1800

GATACACTCT TCGACAATCA ACAATCAAAT ATAAATCAGT ATATCAATTT AGATTCGTAT    1860

ATCTAAGTCT CTTCTATATC CATATTTGAT TTGTTCTCTT TCTGATCAAC TAGATTTATA    1920

ACCTAGATAG ATTTTATAAA TTTAATTTAA TATATATTAC AAAAATGGAC GGTGGTATGT    1980

AATTTATTAC ATTTTATTAT TCTTTGATTA AATTGATGAA TCAATCAATT AATCAATCAA    2040

CCAATCAATT AATCGATCAA TTAATCTCCC GATTCGTCAA TCTCAATGAA GCATCTTGAT    2100

TTAGTTAGTC GATCTCATTA TCGACAGATA TTGTATCAAT CTTTTCAATT GATTTATCAA    2160

ATGGTTTCAT GGAATCCGAT ATTCATCCAT CCATTTGTCG ATTTGATGAG TATTTGATGT    2220

TTTCAATGTT ACATCAATCA AACTGTCAAT TGACCTGTTG AATCAATCAA CTTTTACTAT    2280

CAGCCGGAAA TATATAAACT TTCTCTATTA CAATGATCAA TTGATAATAC ATTAATTTAT    2340

ATTCAATAGA TCATTCAGAT ATCTTTGTCC ATCAAAAATA GAGAAAGATG AAATTGATTT    2400

AAATGGATTG TCCTTTGATT ATTGATTCGG GGTGATTGAT TGTGATTTTA CCTGTGATTT    2460

TTTGATACCT TATTTTTTAA AGTTTCTTAT TACTAACACC TTTTAATAGA AGACGTTGCT    2520

GCTGTATGTA ACATATACTT ACAATTTTCT TTTTCTTTTT TTTCTATTTT GAAAATGATA    2580

GTTGATTTGA TTGATTGCTC TTTCCAATGG ATTTCAGTTC ACGACGCGTT TCAATTATAA    2640

AAGAAAGATG TTATCTTCAT TTAATTCGAT TAATCGATTG ATAAATCACT TAAGATATCA    2700

ATTCATCTAT CAAGATATTG GTTGCTCACC ATTCTAATCA AGCAATCAAT TAATTCAAGT    2760

CAATTCATTT CAAAATATCA TCTTCTAATT CATCATCTAT TGAGATTTTT TAATACTAAC    2820

ATTTTTTTCT TCTTTTTTTT TGTATTTTTA CAGTTAGTTA TTGATAACGG TTCCGGTATG    2880

TGTAAAGCCG GTTTCGCCGG TGATGACGCT CCAAGAGCTG TTTTCCCATC AATTGTTGGT    2940

AGACCAAGAC ATCAAGGTAT CATGGTTGGT ATGGGTCAAA AAGATTCCTA CGTTGGAGAT    3000

GAAGCCCAAT CCAAGAGAGG TATTTTAACT TTAAGATACC CAATTGAACA CGGTATTGTC    3060

ACAAACTGGG ATGATATGGA AAAAATCTGG CATCACACTT TCTACAACGA ATTAAGAGTT    3120

GCCCCAGAAG AACACCCAGT CTTATTAACT GAAGCCCCAA TGAATCCAAA GAACAACAGA    3180

GAAAAGATGA CTCAAATCTT ATTCGAAACT TTCAATGTTC CAGCTTTCTA CGTTTCTATT    3240

CAAGCTGTCT TATCTTTATA CTCTTCTGGT AGAACTACCG GTATTGTTTT AGATTCTGGT    3300

GATGGTGTTA CCCACGTTGT CCCAATTTAC GCTGGTTTCT CCTTACCACA CGCTATCTTA    3360

AGATTAGATT TAGCTGGTAG AGATTTAACT GACTACTTAA TGAAGATCTT ATCTGAAAGA    3420

GGTTACACTT TCTCCACCAC TGCTGAAAGA GAAATTGTTA GAGATATCAA GGAAAAATTA    3480

TGTTACGTTG CTTTAGATTT CGATCAAGAA TTACAAACAT CATCTCAATC TTCTTCTATT    3540

GAAAAATCTT ATGAATTACC AGATGGTCAA GTTATTACCA TTGGTAACGA AGATTCAGA     3600

GCTCCAGAAG CTTTATTCCA CCCATCTGTC TTAGGTTTAG AAGCCTCTGG TATTGATCAA    3660

ACCACTTTCA ACTCCATCAT GAAGTGTGAT GTTGATGTCC GTAAGGAATT ATACGGTAAC    3720

ATTGTTATGT CTGGTGGTAC TACCATGTTC CCAGGTATTG CTGAACGTAT GCAAAAGGAA    3780

ATTACTGCTT TAGCTCCATC TTCCATGAAG GTCAAGATCA TTGCTCCACC AGAAAGAAAG    3840

TACTCCGTTT GGATTGGTGG TTCTATCTTA GCTTCCTTAT CTACTTTCCA ACAAATGTGG    3900

ATTTCAAAGC AAGAATACGA CGAATCAGGA CCATCAATTG TCCACCTCAA GTGTTTCTAA    3960

GGAATTTAAT CATTTTCAAC ATAAAATCTT GTCAATTTTT ATTAAAGTCA TTTTTCATTA    4020

ATCTTTTAAT GTATTCTTTT ATTTGATTTT TCAATATTTC TTGATAAATA AATTTGTTGT    4080

TGAATTTCAT TGATTATTTA TATTTCTTAG ATTTTAAAAA AATATTTTCC TCTTTTTTTA    4140
```

```
TTTTCCTTTG TTTTTCAAAT TTAAAATGAT AGAATGAAAG AATAAAAATA TATATATTAT    4200

TATTATTATT ATTACTGTCA AACGTTTAAA AAGAAGTAGT ATTAAACTTA ACACTCTTCT    4260

GAGTTATAAT GGTAATAACA GTGATTTAAT ATACCTTTTT TTTCCAAATT TTTTTCAATT    4320

ATTCATTTTG GTATTTGGTT AATTATGGTG AATAAAAAAA AAGAAAAATT TCTTGTTTCT    4380

TTTGTTGTTT ATTCTTGTTT TAATTTTTTT TTGTATCAAT CTTTAAATTT AGTTTTAAAT    4440

TTTTTATTAT TATTCTAATT TTAAATTATT AATTGTTGTA ATTAAATTAT TAATTAATTT    4500

CTAATTTTTT TGAACAAAAC GTTTTTATAA TTTTAGAATA TTTAATTAAT TTATTAAATT    4560

TGTTTAAATT GGTATACCAT TTTTTTTTTA CTCTATTTAC CTATTTAATT TTATTATATT    4620

ATTATCGAAA AAAACCTTAA AAAGGACTTC GTAAATTTTA TTGTAATAAA CGCAAAAATG    4680

ACATATATAA GAAAAAAAAT AAAAAGAAAT AAAAAAAACA AGTGGTTGAT TTTACTTTTA    4740

ACTAAGTCAA AGTCTAATAA ATTTCTATTT TTTTTTAAGG AAGAATTAAC TAGATTTATC    4800

AAGTAATCTT TTATCGAT                                                 4818
```

(2) INFORMATION FOR SEQ ID NO:28:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:28:

```
CTGAATTCAA TAAGAGTGTG ATTATATAC                                       29
```

(2) INFORMATION FOR SEQ ID NO:29:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:29:

```
CACCGTCGAC TTTTGTAATA TATATTAAA                                       29
```

(2) INFORMATION FOR SEQ ID NO:30:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:30:

```
GTCGACCTGC AGGGAATTTA ATCATTTTCA AC                                   32
```

(2) INFORMATION FOR SEQ ID NO:31:

(i) SEQUENCE CHARACTERISTICS:
        (A) LENGTH: 32 base pairs
        (B) TYPE: nucleic acid
        (C) STRANDEDNESS: single

```
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:31:

AAGCTTGAAT TCTAAAAAAA AAATGGTATA CC                                32

(2) INFORMATION FOR SEQ ID NO:32:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:32:

ATGATTGAAC AAGATGGATT GC                                          22

(2) INFORMATION FOR SEQ ID NO:33:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:33:

TCAGAAGAAC TCGTCAAGAA GG                                          22

(2) INFORMATION FOR SEQ ID NO:34:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:34:

GCGGCCGCAT GTTTAAATCT GTTGTTTATT CA                               32

(2) INFORMATION FOR SEQ ID NO:35:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:35:

CCCGGGTTAT TGTTTTAATA GGGTATCATT                                  30

(2) INFORMATION FOR SEQ ID NO:36:

(i) SEQUENCE CHARACTERISTICS:
            (A) LENGTH: 19 base pairs
            (B) TYPE: nucleic acid
            (C) STRANDEDNESS: single
```

(D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:36:

GGATTCATTG GGGCTTCAG                                                        19

(2) INFORMATION FOR SEQ ID NO:37:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:37:

TGATTACGAA TTTAATACGA CTCACT                                                26

(2) INFORMATION FOR SEQ ID NO:38:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:38:

CCCCTCGAGG AAATAGATAC ATTACCCAGT GTC                                        33

(2) INFORMATION FOR SEQ ID NO:39:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:39:

CCCCTCGAGT GTCATCGATA TTATGCCCCG CC                                         32

(2) INFORMATION FOR SEQ ID NO:40:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:40:

CCCCTCGAGG CCTTTTTCAC TTGAAACAAT AACTAT                                     36

(2) INFORMATION FOR SEQ ID NO:41:

(i) SEQUENCE CHARACTERISTICS:
        (A) LENGTH: 38 base pairs
        (B) TYPE: nucleic acid
        (C) STRANDEDNESS: single (D) TOPOLOGY: linear (ii) MOLECULE TYPE: other nucleic acid
          (A) DESCRIPTION: /desc = "synthetic DNA"

(xi) SEQUENCE DESCRIPTION: SEQ ID NO:41:

CCCCTCGAGT AATACTAGTC AGATGTTATA ATTATATC                    38

(2) INFORMATION FOR SEQ ID NO:42:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic DNA"

(xi) SEQUENCE DESCRIPTION: SEQ ID NO:42:

CCCCTCGAGT ATCTTTACCA CTATCCAATT AAAATCC                     37

(2) INFORMATION FOR SEQ ID NO:43:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic DNA"

(xi) SEQUENCE DESCRIPTION: SEQ ID NO:43:

CCCCTCGAGT AAAATCCATG GATCAGACGG TAG                         33

(2) INFORMATION FOR SEQ ID NO:44:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic DNA"

(xi) SEQUENCE DESCRIPTION: SEQ ID NO:44:

CCCCTCGAGT AGTTTTTATA TCTGTAACAT CTTAC                       35

(2) INFORMATION FOR SEQ ID NO:45:

(i) SEQUENCE CHARACTERISTICS:
          (A) LENGTH: 46 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic DNA"

(xi) SEQUENCE DESCRIPTION: SEQ ID NO:45:

CCCCTCGAGT AAATTCAACT AAAAATTGAA CTATTTAAAC ACTATG           46

(2) INFORMATION FOR SEQ ID NO:46:

(i) SEQUENCE CHARACTERISTICS:
          (A) LENGTH: 42 base pairs
          (B) TYPE: nucleic acid
          (C) STRANDEDNESS: single (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:46:

CCCCTCGAGA TGATTTCCTT CAATTATATT AAAATCAATT TC                              42

(2) INFORMATION FOR SEQ ID NO:47:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:47:

CAATGAGCCG TTGAATTGAC GAGTG                                                 25

(2) INFORMATION FOR SEQ ID NO:48:

(i) SEQUENCE CHARACTERISTICS:
            (A) LENGTH: 194 base pairs
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (A) ORGANISM: Candida boidinii (xi) SEQUENCE DESCRIPTION: SEQ ID NO:48:

GTAAATTCAA CTAAAAATTG AACTATTTAA ACACTATGAT TTCCTTCAAT TATATTAAAA           60

TCAATTTCAT ATTTCCTTAC TTCTTTTTGC TTTATTATAC ATCAATAACT CAATTAACTC          120

ATTGATTATT TGAAAAAAAA AAACATTTAT TAACTTAACT CCCCGATTAT ATATTATATT          180

ATTGACTTTA CAAA                                                            194

(2) INFORMATION FOR SEQ ID NO:49:

(i) SEQUENCE CHARACTERISTICS:
            (A) LENGTH: 642 base pairs
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (A) ORGANISM: Candida boidinii (xi) SEQUENCE DESCRIPTION: SEQ ID NO:49:

TATCTTTACC ACTATCCAAT TAAAATCCAT GGATCAGACG GTAGTTTTTA TATCTGTAAC           60

ATCTTACTAC TACCACTACT ACTACCACTA CTACTACCAC TACTACTACC ACTACTACTA          120

CTGATAATAA GGTATACTAC ATTTTATCAT ACGTGAAATG TAACGCGTAG ATTAAACATT          180

TTTTTAAAAT TACTGATCAG TACTTTCCAC AATAAGCACT TATTAATATG TGCCTCTTTA          240

AAATTACTTA ATTCCCTTTA CTTTTCATTT TTACAACCGC TTTGGTATTT ACCCCCAGAG          300

TGTTTTAATT GCAATTGAAT TCTTATTTTA ATTTCCATTA CTTTCTTTGT ACCATAATGA          360

AATTGCCGAG TTGTCCCTCC TTTGAATTTA AATCATTCTC TAATATTTAA CTTTAATTTT          420

AATATTTTAG TTATTTATTT GAATTAAAGT AAATTCAACT AAAAATTGAA CTATTTAAAC          480

```
ACTATGATTT CCTTCAATTA TATTAAAATC AATTTCATAT TTCCTTACTT CTTTTTGCTT      540

TATTATACAT CAATAACTCA ATTAACTCAT TGATTATTTG AAAAAAAAAA ACATTTATTA      600

ACTTAACTCC CCGATTATAT ATTATATTAT TGACTTTACA AA                         642
```

(2) INFORMATION FOR SEQ ID NO:50:

(i) SEQUENCE CHARACTERISTICS:
        (A) LENGTH: 839 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Candida boidinii (xi) SEQUENCE DESCRIPTION: SEQ ID NO:50:

```
CTTACATACA TATAGAGTTT GAAATAGATA CATTACCCAG TGTCATCGAT ATTATGCCCC       60

GCCTTTTTCA CTTGAAACAA TAACTATTAT TACTACTATT ATTATTTCTA TTCATATATC      120

CTAAAAATTA TATTAAAATT GGCTCTTTTA TGCAAAAAAT GTACATTTAT GGTAATACTA      180

GTCAGATGTT ATAATTATAT CTTTACCACT ATCCAATTAA AATCCATGGA TCAGACGGTA      240

GTTTTTATAT CTGTAACATC TTACTACTAC CACTACTACT ACCACTACTA CTACCACTAC      300

TACTACCACT ACTACTACTG ATAATAAGGT ATACTACATT TTATCATACG TGAAATGTAA      360

CGCGTAGATT AAACATTTTT TTAAAATTAC TGATCAGTAC TTTCCACAAT AAGCACTTAT      420

TAATATGTGC CTCTTTAAAA TTACTTAATT CCCTTTACTT TTCATTTTTA CAACCGCTTT      480

GGTATTTACC CCCAGAGTGT TTTAATTGCA ATTGAATTCT TATTTTAATT TCCATTACTT      540

TCTTTGTACC ATAATGAAAT TGCCGAGTTG TCCCTCCTTT GAATTAAAAT CATTCTCTAA      600

TATTTAACTT TAATTTTAAT ATTTTAGTTA TTTATTTGAA TTAAAGTAAA TTCAACTAAA      660

AATTGAACTA TTTAAACACT ATGATTTCCT TCAATTATAT TAAAATCAAT TTCATATTTC      720

CTTACTTCTT TTTGCTTTAT TATACATCAA TAACTCAATT AACTCATTGA TTATTTGAAA      780

AAAAAAAACA TTTATTAACT TAACTCCCCG ATTATATATT ATATTATTGA CTTTACAAA      839
```

(2) INFORMATION FOR SEQ ID NO:51:

(i) SEQUENCE CHARACTERISTICS:
        (A) LENGTH: 364 amino acids
        (B) TYPE: amino acid
        (D) TOPOLOGY: linear (ii) MOLECULE TYPE: protein (xi) SEQUENCE DESCRIPTION: SEQ ID NO:51:

```
Met Lys Ile Val Leu Val Leu Tyr Asp Ala Gly Lys His Ala Ala Asp
 1               5                  10                  15

Glu Glu Lys Leu Tyr Gly Cys Thr Glu Asn Lys Leu Gly Ile Ala Asn
                20                  25                  30

Trp Leu Lys Asp Gln Gly His Glu Leu Ile Thr Thr Ser Asp Lys Glu
            35                  40                  45

Gly Glu Thr Ser Glu Leu Asp Lys His Ile Pro Asp Ala Asp Ile Ile
        50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Val Ala Gly Val Gly Ser Asp
                85                  90                  95
```

```
His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
            115                 120                 125

Met Thr Met Leu Val Leu Val Arg Asn Phe Val Pro Ala His Glu Gln
            130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
            165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Glu Lys Val Gly
            195                 200                 205

Ala Arg Arg Val Glu Asn Ile Glu Glu Leu Val Ala Gln Ala Asp Ile
            210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Ala Leu Glu
                260                 265                 270

Ser Gly Gln Leu Arg Gly Tyr Gly Gly Asp Val Trp Phe Pro Gln Pro
            275                 280                 285

Ala Pro Lys Asp His Pro Trp Arg Asp Met Arg Asn Lys Tyr Gly Ala
            290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
                340                 345                 350

Tyr Val Thr Lys Ala Tyr Gly Lys His Asp Lys Lys
            355                 360
```